United States Patent
Jain et al.

(10) Patent No.: US 11,103,503 B2
(45) Date of Patent: *Aug. 31, 2021

(54) PHARMACEUTICAL COMPOSITIONS OF LURASIDONE

(71) Applicant: SLAYBACK PHARMA LLC, Princeton, NJ (US)

(72) Inventors: Paras P. Jain, Maharashtra (IN); Ajay Kumar Singh, Princeton, NJ (US); Praveen Kumar Subbappa, Princeton, NJ (US); Keerthi Priya, Telangana (IN); Girish Kumar Jain, Maharashtra (IN); Girish G. Kore, Maharashtra (IN); Hanimi Reddy Bapatu, Telangana (IN); Sandeep Jain, Madhya Pradesh (IN)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/774,457

(22) Filed: Jan. 28, 2020

(65) Prior Publication Data

US 2020/0222395 A1 Jul. 16, 2020

Related U.S. Application Data

(63) Continuation of application No. 16/697,415, filed on Nov. 27, 2019.

(30) Foreign Application Priority Data

Jan. 10, 2019 (IN) .............................. 201941001273
Jan. 18, 2019 (IN) .............................. 201941002316

(51) Int. Cl.
 *A61K 31/496* (2006.01)
 *A61K 9/20* (2006.01)
 *A61K 47/38* (2006.01)
 *A61K 47/32* (2006.01)

(52) U.S. Cl.
 CPC .......... *A61K 31/496* (2013.01); *A61K 9/2009* (2013.01); *A61K 9/2054* (2013.01); *A61K 47/32* (2013.01); *A61K 47/38* (2013.01)

(58) Field of Classification Search
 CPC .. A61K 31/496; A61K 9/2009; A61K 9/2054; A61K 47/32; A61K 47/38
 See application file for complete search history.

(56) References Cited

U.S. PATENT DOCUMENTS

| | | | |
|---|---|---|---|
| 9,433,620 B2 * | 9/2016 | Khera | A61K 31/496 |
| 2014/0343076 A1 | 11/2014 | Kulkarni et al. | |
| 2015/0157628 A1 | 6/2015 | Kannusamy et al. | |
| 2019/0321304 A1 | 10/2019 | Xu et al. | |

FOREIGN PATENT DOCUMENTS

| | | |
|---|---|---|
| CN | 102078309 A | 6/2011 |
| CN | 105395493 A | 3/2016 |
| CN | 106539769 A | 3/2017 |
| WO | WO 2011/085188 A1 | 7/2011 |
| WO | WO 2012/063246 A1 | 5/2012 |
| WO | WO 2013/132511 A1 | 9/2013 |
| WO | WO 2014/076712 A2 | 5/2014 |
| WO | WO 2018/127088 A1 | 7/2018 |
| WO | WO 2019/128991 A1 | 7/2019 |

OTHER PUBLICATIONS

International Search Report and Written Opinion of the International Searching Authority for International Application No. PCT/US 20/16728, dated May 13, 2020.

* cited by examiner

*Primary Examiner* — Robert A Wax
*Assistant Examiner* — Olga V. Tcherkasskaya
(74) *Attorney, Agent, or Firm* — Birch, Stewart, Kolasch & Birch, LLP

(57) ABSTRACT

Solid dispersions of lurasidone or a pharmaceutically acceptable salt thereof are described, as well as pharmaceutical formulations thereof, and methods for making such formulations. Preferably, the solid dispersions are prepared by hot-melt extrusion or spray-drying, and comprise lurasidone with a pharmaceutically acceptable carrier (e.g., hydroxypropyl methyl cellulose acetate succinate (HPMC-AS), polyvinyl pyrrolidine vinyl acetate (PVP/VA) copolymer, hydroxypropyl methylcellulose phthalate (HPMCP), or mixtures thereof). The pharmaceutical composition may be orally administered to a patient in either the fed or fasted state, with a decrease or elimination of the food effect. Preferably, following oral administration of the pharmaceutical compositions, there is no substantial difference in the pharmacokinetic parameters (e.g., $T_{max}$, $C_{max}$, $AUC_{0-t}$ and/or $AUC_{0-infinity}$) of lurasidone, regardless of whether the pharmaceutical compositions are administered to a subject in the fed or fasted state.

12 Claims, 11 Drawing Sheets

PHARMACEUTICAL COMPOSITIONS OF LURASIDONE

CROSS-REFERENCE TO RELATED APPLICATIONS

This application is a continuation of U.S. patent application Ser. No. 16/697,415, filed on Nov. 27, 2019, which claims foreign priority to Indian Application Nos. IN 201941001273 and IN 201941002316, filed on Jan. 10, 2019 and Jan. 18, 2019, respectively, each of which is incorporated by reference in its entirety.

FIELD OF THE INVENTION

The present application relates to pharmaceutical compositions comprising a lurasidone solid dispersion (e.g., an amorphous lurasidone solid dispersion) and pharmaceutically acceptable excipient(s), as well as methods for making such pharmaceutical compositions. The compositions may be administered in either the fed or fasted state. Advantageously, the pharmaceutical compositions according to the invention reduce or eliminate the food effect, which has been reported in connection with prior art formulations, e.g., as associated with the commercially-available lurasidone drug product sold under the trademark LATUIDA®.

The present application also provides methods for treating CNS disorders in a human, including schizophrenia and depressive episodes associated with bipolar disorder.

BACKGROUND OF THE INVENTION

Lurasidone is an antagonist with high affinity binding at the dopamine D2 receptors, serotonin 5-HT2A and 5-HT7 receptors. Lurasidone has the chemical name N-4-4-(1,2-benzisothiazol-3-yl)-1-piperazinyl-(2R,3R)-2,3-tetramethylene-butyl-(1R,2S,3R,4'S)-2,3-bicyclo[2.2.1]heptanedicarboxyimide, and has the structural formula (I), shown below:

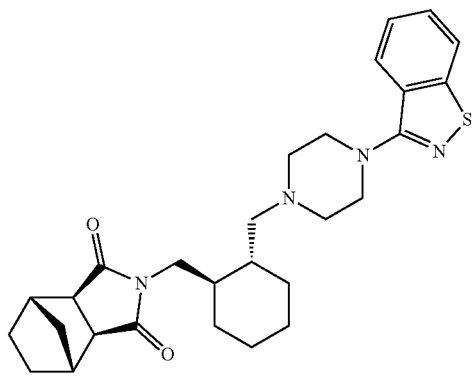 [SMILES: O=C1[C@@H]2[C@H]3CC[C@H](C3)[C@@H]2C(=O)N1C[C@@H]1CCCC[C@H]1CN1CCN(c2nsc3ccccc23)CC1]

Formula (I)

Lurasidone, in the form of a free base or as an acid addition salt, is known to have psychotropic activities and is effective as a therapeutic agent, particularly for schizophrenia or senile dementia. Senile dementia is broadly classified into Alzheimer's dementia and cerebrovascular dementia, and it can be said that the two make up about 80% of senile dementia.

Lurasidone is very slightly soluble in water. Attaining sufficient bioavailability of this drug is problematic. It is estimated that about 9-19% of an administered dose is absorbed in the fed state.

The commercially-available lurasidone drug product sold under the trademark LATUDA® is provided as 20 mg, 40 mg, 60 mg, 80 mg and 120 mg tablets for oral administration. LATUDA® must be administered with food (at least 350 calories), which substantially increases the absorption, e.g., mean $C_{max}$ and AUC values are increased by about 3-times and 2-times, respectively, when administered with food compared to the levels observed under fasting conditions.

Weight gain is a common adverse effect associated with atypical antipsychotic drugs. As the commercially-available lurasidone drug product sold under the trademark LATUDA® must be administered with food (at least 350 calories), this further increases the weight gain adverse effect.

There remains a need for a composition and a dosage form exhibiting suitable bioavailability, which substantially reduces or overcomes the differential between the bioavailability of the drug in patients who are fasted versus the bioavailability of the drug in patients who are fed, and/or which substantially can reduce or overcome the intra- and/or inter-individual variations observed with the commercial available products.

Thus, there exists a need for the development of pharmaceutical lurasidone compositions, as well as methods of treatment, which successfully address or eliminate the food effect and/or provide improved bioavailability.

SUMMARY OF THE INVENTION

The present application relates to pharmaceutical compositions of lurasidone that decrease or eliminate the food effect, which has been problematic with prior lurasidone formulations, such as the commercially-available lurasidone drug product sold under the trademark LATUIDA® oral tablet drug product. In particular, the present application relates to pharmaceutical compositions comprising lurasidone solid dispersion and pharmaceutically acceptable excipient(s), wherein the composition may be administered in either fed or fasted state, and wherein the food effect is decreased or eliminated.

Certain aspects relate to compositions for oral administration that provide higher lurasidone bioavailability than commercially available lurasidone formulations sold under the trademark LATUIDA® in both a fed and fasted state, e.g., compositions that yield higher plasma levels in both a fed and a fasted state.

Specifically, the present application also provides compositions for oral administration that provide a therapeutically acceptable plasma level of lurasidone when administered to a patient in a fasted state. Thus, in certain aspects, the present application relates to improved lurasidone pharmaceutical compositions, which exhibit improved bioavailability in the fasting state, compared to the existing formulations, e.g., such as the commercially-available lurasidone drug product sold under the trademark LATUIDA® oral tablet drug product.

In certain embodiments, upon oral administration to a patient, the pharmaceutical compositions described herein exhibit less variability in pharmacokinetic parameters (e.g., $T_{max}$, $C_{max}$, $AUC_{0-t}$ and/or $AUC_{0\text{-}infinity}$) between the fasted and fed states. For example, certain embodiments relate to compositions for oral administration that provide lurasidone to a patient population with lower variability in bioavailability (e.g., a narrower observed range for $C_{max}$ and AUC values), thus providing consistent pharmacokinetic (PK) parameters across a patient population to whom the formulation is administered.

In certain aspects, the application describes lurasidone compositions that are suitable for oral administration to patients, and which provide uniform plasma level(s) and therapeutically effective lurasidone exposure, in fasted and/or fed states. The application also provides lurasidone compositions that exhibit less intra-subject variability and/or less inter-subject variability in pharmacokinetic parameters (e.g., $T_{max}$, $C_{max}$, $AUC_{0-t}$ and/or $AUC_{0-infinity}$) than commercially available lurasidone formulations, e.g., such as the commercially-available lurasidone drug product sold under the trademark LATUIDA®.

Preferably, following oral administration of said pharmaceutical composition to subjects, there is no substantial difference in the pharmacokinetic parameters (e.g., $T_{max}$, $C_{max}$, $AUC_{0-t}$ and/or $AUC_{0-infinity}$) of the lurasidone, regardless of whether the pharmaceutical composition is administered to a subject in fed or fasted state. By "no substantial difference" is meant that the values for the pharmacokinetic parameters (e.g., $T_{max}$, $C_{max}$, $AUC_{0-t}$ and/or $AUC_{0-infinity}$) are within about 70% to about 143% of each other, preferably within about 80 to about 125%.

The present invention provides a method for treatment or prevention of CNS disorders, which comprises administering a solid oral dosage form comprising an effective amount of lurasidone to a human in fasted state, wherein the area under the plasma concentration versus time curve ($AUC_{0-inf}$) of the lurasidone in the human subsequent to said administering is from 70% to 143% of the mean area under the lurasidone plasma concentration versus time curve ($AUC_{0-inf}$) resulting from administration of control lurasidone oral tablets containing the same amount of lurasidone to a cohort of humans in a fed state.

In one embodiment, the present invention provides a method for treatment or prevention of a CNS disorder, which method comprises (a) providing a pharmaceutical composition of lurasidone as described in the present specification to a human without regard to food, e.g., wherein the pharmaceutical compositions do not have a food effect; and (b) administering said pharmaceutical composition to a human, in need thereof, without regard to food.

In an embodiment, the invention relates to a pharmaceutical composition comprising a solid dispersion of amorphous lurasidone in a pharmaceutically acceptable carrier, wherein the pharmaceutically acceptable carrier is a polymer selected from the group consisting of hydroxypropyl methyl cellulose acetate succinate (HPMC-AS), polyvinyl pyrrolidine vinyl acetate (PVP/VA) copolymer, hydroxypropyl methylcellulose phthalate (HPMCP), and mixtures thereof; and wherein the pharmaceutical composition may be administered to a human subject in either fed or fasted state.

In an embodiment, pharmaceutical compositions are provided, wherein at least one pharmacokinetic parameter in the fasted stated is from about 70% to about 143% of the at least one pharmacokinetic parameter in the fed state; and wherein the at least one pharmacokinetic parameter is selected from (i) the area under the plasma concentration versus time curve for total drug exposure ($AUC_{0-infinity}$), (ii) peak plasma concentration ($C_{max}$), (iii) time to reach $C_{max}$ ($T_{max}$), (iv) area under the plasma concentration versus time curve at a certain time (t) after drug administration ($AUC_{0-t}$), or (v) combinations thereof.

In an embodiment, pharmaceutical compositions comprising a solid dispersion of amorphous lurasidone in a pharmaceutically acceptable carrier are provided, wherein the pharmaceutically acceptable carrier further comprises a solubilizer, a surfactant, or a mixture thereof, and wherein the pharmaceutical composition may be administered to a human subject in either fed or fasted state.

In an embodiment, pharmaceutical compositions comprising a solid dispersion of amorphous lurasidone in at least one pharmaceutically acceptable carrier are provided, wherein the in vitro dissolution rate is less than about 50% in 60 minutes, and wherein the in vitro release rate is chosen such that the peak plasma levels of lurasidone obtained in vivo occurs between about 1 and about 6 hours after administration of the composition to a patient. For example, the in vitro dissolution rate may be determined using a USP paddle method of 75 rpm in 500 mL 0.1 N HCl at 37° C., or the in vitro dissolution rate may be determined using a USP paddle method of 75 rpm in 1000 ml 4.5 pH acetate buffer at 37° C.

In an embodiment, pharmaceutical compositions comprising a solid dispersion of amorphous lurasidone in a pharmaceutically acceptable carrier are provided, wherein at least one parameter in the fasted stated is from about 70% to about 143% of the at least one pharmacokinetic parameter in the fed state; and wherein the at least one pharmacokinetic parameter is selected from $AUC_{0-infinity}$, $C_{max}$, $T_{max}$, $AUC_{0-t}$, or combinations thereof.

In an embodiment, pharmaceutical compositions comprising a solid dispersion of amorphous lurasidone in a pharmaceutically acceptable carrier are provided, wherein the solid dispersion optionally further comprises a solubilizer, a surfactant, or a mixture thereof, wherein said composition upon oral administration in fasting and fed states exhibits bioequivalence to a commercially available reference lurasidone drug product (such as LATUDA®), in the fed state, and wherein said bioequivalence is established by at least one parameter that is selected from (i) a confidence interval for mean $AUC_{0-t}$ between about 70% and about 143%; (ii) a confidence interval for mean $AUC_{0-infinity}$ between about 70% and about 143%; (iii) a confidence interval for mean $C_{max}$ between about 70% and about 143%; (iv) a confidence interval for mean $T_{max}$ between about 70% and about 143%; or (v) combinations thereof. Preferably, bioequivalence is established by at least one parameter that is selected from (i) a confidence interval for mean $AUC_{0-t}$ between about 80% and about 125%; (ii) a confidence interval for mean $AUC_{0-infinity}$ between about 80% and about 125%; (iii) a confidence interval for mean $C_{max}$ between about 80% and about 125%; (iv) a confidence interval for mean $T_{max}$ between about 80% and about 125%; or (v) combinations thereof.

Each of embodiments above may further have one or more of the following additional elements in any combination:

Element 1: a pharmaceutical composition as described herein, which comprises a solid dispersion of amorphous lurasidone that is made by hot-melt extrusion, spray-drying or co-precipitation.

Element 2: a pharmaceutical composition as described herein, wherein the solid dispersion of amorphous lurasidone has a weight ratio of the lurasidone or pharmaceutically acceptable salt thereof to the pharmaceutically acceptable carrier from about 1:1 to about 1:6, preferably from about 1:2 to about 1:4, most preferably about 1:3.

Element 3: a pharmaceutical composition as described herein, wherein the pharmaceutical composition comprises from about 50 mg to about 400 mg of the lurasidone or pharmaceutically acceptable salt thereof, preferably 20 mg, 40 mg, 60 mg, 80 mg, 120 mg or 160 mg of lurasidone hydrochloride, or 18.62 mg, 37.24 mg, 55.87 mg, 74.49 mg or 111.74 mg of lurasidone free base.

Element 4: a pharmaceutical composition as described herein, wherein the pharmaceutical composition is in the form of a tablet, a capsule, a caplet, beads, granules or oral suspension.

Element 5: a pharmaceutical composition as described herein, wherein the pharmaceutical composition comprises granules of the solid dispersion of amorphous lurasidone, and wherein the granules of the solid dispersion of amorphous lurasidone comprise lurasidone and HPMC-AS as a pharmaceutically acceptable carrier.

Element 6: a pharmaceutical composition as described herein, wherein the pharmaceutical composition comprises granules of the solid dispersion of amorphous lurasidone, and wherein the granules of the solid dispersion of amorphous lurasidone comprise at least a first portion of granules comprising lurasidone and HPMC-AS, and at least a second portion of granules comprising lurasidone and PVP/VA copolymer.

Element 7: a pharmaceutical composition as described herein, wherein the pharmaceutical composition comprises granules of the solid dispersion of amorphous lurasidone, and further comprising at least one extra-granular excipient selected from the group consisting of microcrystalline cellulose, croscarmellose sodium (Ac-Di-Sol), colloidal silicon dioxide, and mixtures thereof; preferably wherein the at least one extra-granular excipient comprises microcrystalline cellulose, croscarmellose sodium (Ac-Di-Sol), or mixtures thereof. More preferably, the at least one extra-granular excipient consists essentially of, or consists of, microcrystalline cellulose, croscarmellose sodium (Ac-Di-Sol), and colloidal silicon dioxide and/or the at least one extra-granular excipient consists essentially of, or consists of, microcrystalline cellulose and croscarmellose sodium (Ac-Di-Sol).

Element 8: a pharmaceutical composition as described herein, wherein the pharmaceutical composition comprises granules of the solid dispersion of amorphous lurasidone, and wherein the granules further comprise at least one intra-granular excipient, preferably wherein the at least one intra-granular excipient comprises microcrystalline cellulose, croscarmellose sodium (Ac-Di-Sol), colloidal silicon dioxide, or mixtures thereof. Preferably, the at least one intra-granular excipient consists essentially of, or consists of microcrystalline cellulose, croscarmellose sodium (Ac-Di-Sol), and colloidal silicon dioxide.

Element 9: a pharmaceutical composition as described herein, which is obtained by direct compression, wet granulation or dry granulation.

Element 10: a pharmaceutical composition as described herein further comprising at least one excipient selected from the group consisting of diluents, binders, chelating agents, coating agents, disintegrating agents, lubricants, colorants, surfactants and mixtures thereof. These pharmaceutically acceptable excipients may be used in intra-granular or extra-granular portions.

Element 11: a method for treating a CNS disorder in a human, which method comprises administering a pharmaceutical composition as described herein to a patient in a fasted or fed state.

Element 12: a pharmaceutical composition as described herein, wherein the pharmaceutical composition is in the form of a tablet, and wherein the tablet comprises (a) granules of the solid dispersion of amorphous lurasidone, (b) at least one extra-granular excipient, and (c) optionally, a tablet coating.

Element 13: a pharmaceutical composition as described herein, wherein the pharmaceutical composition comprises granules of a solid dispersion of amorphous lurasidone, and wherein the granules comprise lurasidone, hydroxypropyl methyl cellulose acetate succinate (HPMC-AS), hydroxypropyl cellulose (HPC), optionally sodium lauryl sulfate, and mixtures thereof. Preferably, the granules consist essentially of, or consist of, lurasidone, hydroxypropyl methyl cellulose acetate succinate (HPMC-AS), hydroxypropyl cellulose (HPC), and optionally, sodium lauryl sulfate.

Element 14: a pharmaceutical composition as described herein, wherein the pharmaceutical composition comprises granules of a solid dispersion of amorphous lurasidone, and wherein the granules comprise lurasidone, hydroxypropyl methyl cellulose acetate succinate (HPMC-AS), hydroxypropyl cellulose (HPC), and optionally, sodium lauryl sulfate, and wherein the composition further comprises an extra-granular portion containing hydroxypropyl methyl cellulose acetate succinate (HPMC-AS), wherein the composition may be administered in the fed and/or fasted state.

Element 15: a pharmaceutical composition as described herein, wherein the pharmaceutical composition comprises granules of a solid dispersion of amorphous lurasidone, wherein the granules comprise lurasidone and hydroxypropyl methyl cellulose acetate succinate (HPMC-AS), and wherein the composition further comprises an extra-granular portion containing hydroxypropyl methyl cellulose acetate succinate (HPMC-AS), wherein the composition may be administered in the fed and/or fasted state.

Element 16: a pharmaceutical composition as described herein, wherein the pharmaceutical composition comprises granules of a solid dispersion of amorphous lurasidone, and further comprises at least one extra-granular excipient selected from the group consisting of microcrystalline cellulose, croscarmellose sodium (Ac-Di-Sol), colloidal silicon dioxide, and mixtures thereof.

Element 17: a pharmaceutical composition as described herein, wherein the $AUC_{0-infinity}$ of lurasidone in a human subject subsequent to administration in the fasted state is from about 70% to about 143% of the $AUC_{0-infinity}$ of lurasidone in a human subject subsequent to administration in the fed state, preferably wherein the $AUC_{0-infinity}$ of lurasidone in a human subject subsequent to administration in the fasted state is from about 80% to about 125% of the $AUC_{0-infinity}$ of lurasidone in a human subject subsequent to administration in the fed state. Also covered is a pharmaceutical composition as described herein, wherein the $AUC_{0-t}$ of lurasidone in a human subject subsequent to administration in the fasted state is from about 70% to about 143% of the $AUC_{0-t}$ of lurasidone in a human subject subsequent to administration in the fed state, preferably wherein the $AUC_{0-t}$ of lurasidone in a human subject subsequent to administration in the fasted state is from about 80% to about 125% of the $AUC_{0-t}$ of lurasidone in a human subject subsequent to administration in the fed state.

Element 18: a pharmaceutical composition as described herein, wherein the $C_{max}$ of lurasidone in a human subject subsequent to administration in fasted state is from about 70% to about 143% of the $C_{max}$ of lurasidone in a human subject subsequent to administration in the fed state, preferably wherein the $C_{max}$ of lurasidone in a human subject subsequent to administration in fasted state is from about 80% to about 125% of the $C_{max}$ of lurasidone in a human subject subsequent to administration in the fed state. Also covered is a pharmaceutical composition as described herein, wherein the $T_{max}$ of lurasidone in a human subject subsequent to administration in fasted state is from about 70% to about 143% of the $T_{max}$ of lurasidone in a human subject subsequent to administration in the fed state, preferably wherein the $T_{max}$ of lurasidone in a human subject subsequent to administration in fasted state is from about 80% to about 125% of the $T_{max}$ of lurasidone in a human subject subsequent to administration in the fed state.

Element 19: a pharmaceutical composition as described herein, wherein said composition upon oral administration in fasting and fed states exhibits bioequivalence to a commercially available reference lurasidone drug product (such as LATUDA®), in the fed state, and wherein said bioequivalence is established by at least one of: (i) a confidence interval for mean $AUC_{0-t}$ between about 70% and about 143%; (ii) a confidence interval for mean $AUC_{0\text{-}infinity}$ between about 70% and about 143%; (iii) a confidence interval for mean $C_{max}$ between about 70% and about 143%; (iv) a confidence interval for mean $T_{max}$ between about 70% and about 143%; or combinations thereof.

Element 20: A pharmaceutical composition as described herein, wherein the percentage loading of the lurasidone in the solid dispersion is from about 10% (w/w) to about 80% (w/w), preferably from about 20% (w/w) to about 70% (w/w), or from about 30% (w/w) to about 60% (w/w).

Element 21: A pharmaceutical composition as described herein, wherein the weight ratio of the lurasidone in the solid dispersion to the pharmaceutically acceptable carrier in the solid dispersion is from about 1:1 to about 1:10, preferably from about 1:3 to about 1:5.

Element 22: A method for reducing the food effect exhibited by lurasidone following administration to a subject, said method comprising administration of a unit dosage form comprising a pharmaceutical composition as described herein.

Element 23: A method for preparing a pharmaceutical composition as described herein, which comprises preparing a mixture (e.g., a liquid mixture) or a solution including lurasidone or a pharmaceutically acceptable salt thereof, and a pharmaceutically acceptable carrier (e.g., a matrix polymer); and spray drying the mixture or the solution to form a solid dispersion (e.g., a spray dried dispersion).

Element 24: A method for preparing a pharmaceutical composition as described herein, which comprises preparing a mixture of lurasidone or a pharmaceutically acceptable salt thereof, and a pharmaceutically acceptable carrier; heating (e.g., up to or above the transition glass temperature or melting temperature of the matrix polymer) the mixture to form a homogenous molten mass; extruding the molten mass; and cooling the molten mass to form a solid dispersion (e.g., a hot melt extrusion).

Element 25: A pharmaceutical composition as described herein, wherein following administration of said pharmaceutical composition to subjects, the ratio of the mean bioavailability for fed subjects to the mean bioavailability for fasted subjects is from about 1.0 to about 2.0.

Element 26: A pharmaceutical composition as described herein, wherein following administration of said pharmaceutical composition to subjects in fasted state, the mean bioavailability is greater than 20% in fasted state.

Element 27: A pharmaceutical composition as described herein, wherein administration of said pharmaceutical composition to fed and fasted subjects produces a coefficient of variation in $C_{max}$ of less than about 60%; or wherein administration of pharmaceutical composition to fasted subjects produces a coefficient of variation in $C_{max}$ of less than about 65%; or wherein administration of said pharmaceutical composition to fed subjects produces a coefficient of variation in $C_{max}$ of less than about 65%.

Element 28: A pharmaceutical composition as described herein, wherein administration of said pharmaceutical composition to fed and fasted subjects produces a coefficient of variation in $AUC_\infty$ of less than about 60%; or wherein administration of said pharmaceutical composition to fasted subjects produces a coefficient of variation in $AUC_\infty$ of less than about 65%; or wherein administration of said pharmaceutical composition to fed subjects produces a coefficient of variation in $AUC_\infty$ of less than about 65%.

By way of non-limiting example, exemplary combinations applicable to the embodiments described in this application may include any combination with one or more of Elements 1-28, described above.

DETAILED DESCRIPTION OF THE INVENTION

Figure 1:
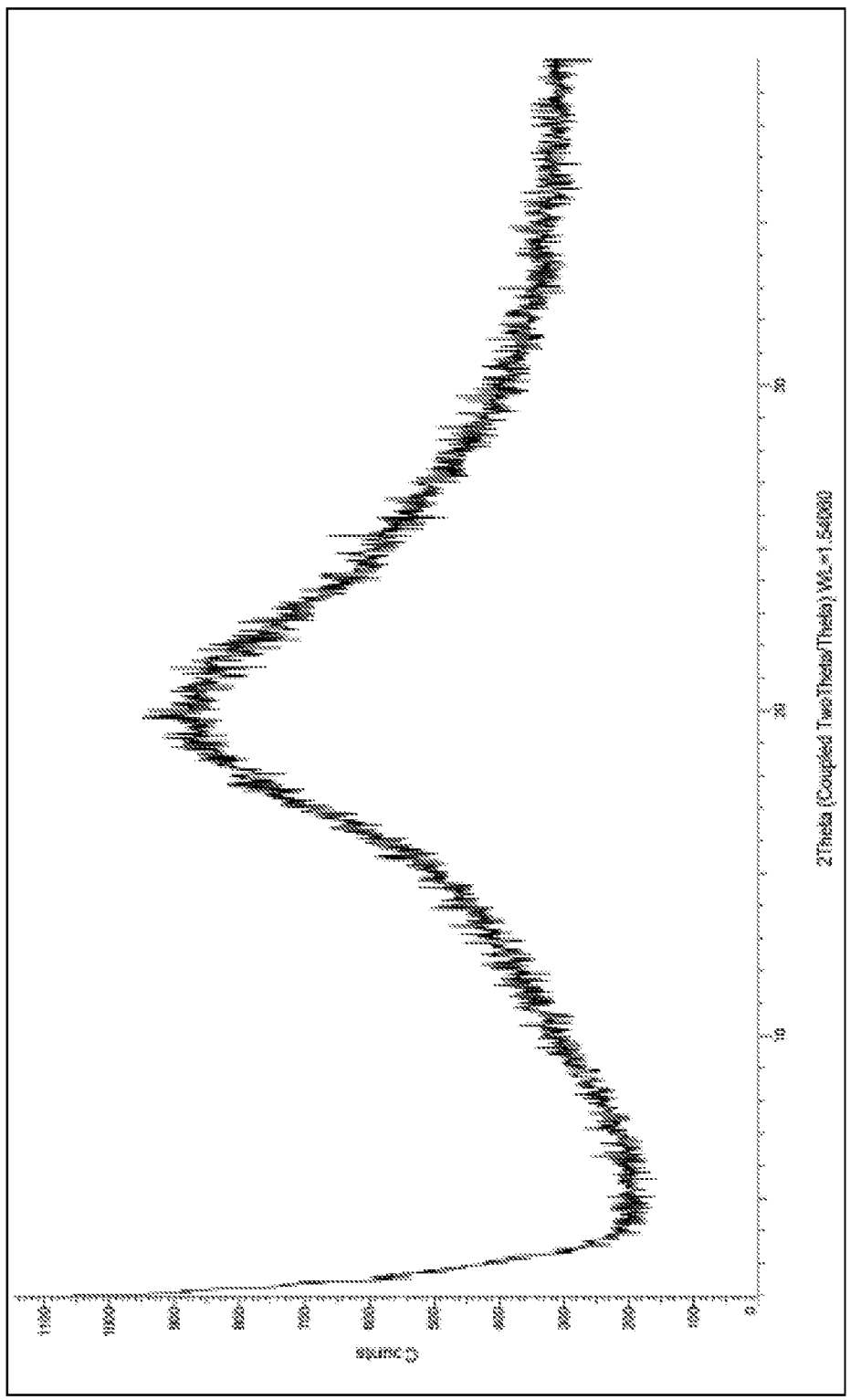
FIG. 1 is the Powder X-Ray Diffraction (PXRD) pattern of the solid dispersion composition corresponding to extrudate 1 in Composition 1 (in Example 1).

Pharmaceutical compositions according to the invention may improve the absorption of lurasidone in the human body, and increase the absorption and bioavailability of the drug in comparison to the commercially available oral formulations.

Unless defined otherwise, all the technical and scientific terms used herein have the same meanings as commonly known by a person skilled in the art. In the case that there is a plurality of definitions for the terms herein, the definitions provided herein will prevail.

As used herein the term "lurasidone" refers to lurasidone free base or a pharmaceutically acceptable salt, solvate or hydrate thereof. In certain aspects, lurasidone free base or lurasidone hydrochloride may be used. Any crystalline form of lurasidone as well as the amorphous form may be used for the preparation of the pharmaceutical compositions of the present invention. In a preferred embodiment, lurasidone in amorphous form is used. In a preferred embodiment, the solid dispersions of lurasidone comprise the amorphous form of lurasidone.

The term "pharmaceutically acceptable" includes those substances, which, according to a common medical judgment, are suitable to be in contact with a tissue of a patient without any inappropriate toxicity, irritation, allergic response, etc., have a reasonable balance between advantages and disadvantages, and can be applied to its target use effectively.

The terms "pharmaceutical composition," "pharmaceutical product," "pharmaceutical dosage form," "dosage form," "pharmaceutical formulation," etc., refer to a pharmaceutical composition that may be administered to a patient in need of treatment, which may be in any conventional formulation, e.g., in the form of a powder, a granule, a pill, a capsule, a tablet, a solution, a suspension, or a patch, etc.

By "solid dispersion" is meant a molecular dispersion of a compound, particularly a drug substance within a polymer or carrier. The term solid dispersion in general means a system in solid state comprising at least two components, wherein one component is dispersed substantially evenly throughout the other component(s). For example, solid dispersions may be the dispersion of one or more active ingredients in an inert carrier or matrix at solid state, prepared by the melting, solvent, or melting-solvent methods. While not wishing to be bound by theory, in a solid dispersion, the drug may be present in a molecular state, colloidal state, metastable state, or an amorphous state. Formation of a molecular dispersion may provide a means of reducing the particle size to nearly molecular levels (i.e., there are no particles). As the polymer dissolves, the drug is exposed to the dissolution media as fine particles, which are amorphous, and which can dissolve and be absorbed more rapidly than larger particles.

In certain aspects, the solid dispersions comprise an amorphous lurasidone drug substance and at least one or more polymers or carriers. By "amorphous drug substance," is meant that the amorphous solid contains drug substance in a substantially amorphous solid-state form, e.g., at least about 80% of the drug substance in the dispersion is in an amorphous form, more preferably at least about 90% of the drug substance in the dispersion is in an amorphous form, and most preferably at least about 95% of the drug substance in the dispersion is in amorphous form.

The term "bioavailability" indicates the extent to which a drug or another substance is utilized by a target tissue after administration. For example, "bioavailability" may refer to the fraction of drug absorbed following administration to a subject or patient under a fasted state. In certain aspects, under fasted state, the bioavailability of lurasidone when formulated as described herein is at least about 15%, but may be greater than 20%, 25%, 30%, 35%, 40%, 45%, or 50% of the dose administered. As used herein, the term "improved bioavailability" refers to the increase in concentration of a drug in the body fluid provided by the compositions of the present invention in the fasted state.

The term "in vivo" in general means in the living body of a plant or animal, whereas the term "in vitro" generally means outside the body and in an artificial environment.

By "coefficient of variation" is meant the arithmetic standard deviation divided by the arithmetic mean for a particular pharmacokinetic parameter, where the data is obtained from a pharmacokinetic study involving 10, 12, or more subjects or patients.

By "mean" is meant the arithmetic mean for a particular pharmacokinetic parameter, where the data is obtained from a pharmacokinetic study involving 10, 12, or more subjects or patients.

The term "peak plasma drug concentration ($C_{max}$)" means the maximum plasma drug concentration attained after drug administration, e.g., the mean peak concentration of a drug achieved in plasma after dosing.

The term "peak time of plasma drug concentration ($T_{max}$)" means the time when peak plasma drug concentration ($C_{max}$) is attained after drug administration.

The terms "$AUC_{0-infin}$," "$AUC_\infty$," "$AUC_{0-\infty}$," or "Area Under the Curve$_\infty$," means the area under a plasma drug concentration-time curve from time point of 0 to infinity after drug administration, e.g., the mean integrated area under the curve for the plasma concentration of a drug, versus time from t=0 to $\infty$ following dosing. The term "$AUC_{0-t}$," means the area under a plasma drug concentration-time curve from time point of 0 to t after drug administration.

Certain embodiments relate to pharmaceuticals compositions as described herein, which are stable, e.g., stable over the shelf life of the drug product. As used herein, the term "stable" is defined as no more than about 5% loss of lurasidone under typical commercial storage conditions. In certain embodiments, the formulations of the present invention will have no more than about 3% loss of lurasidone, more preferably, no more than about 2% loss of lurasidone, under typical commercial storage conditions. The composition retains at least about 95% of the potency of lurasidone after storing the composition at 40° C. and 75% relative humidity for at least three months. In certain aspects, the term "stable" refers to chemical stability, wherein not more than 1.5% w/w of total related substances are formed on storage at accelerated conditions of stability at 40° C. and 75% relative humidity or at 25° C. and 60% relative humidity for a period of at least three months or to the extent necessary for use of the composition.

Reference throughout this specification will be made to the administration of a pharmaceutical composition under fed or fasted conditions. It is well understood in the art that the pharmacokinetic performance of some compositions is affected by the presence or absence of food in the gastrointestinal system, which is referred to in the art as "fed" or "fasted" states.

For example, the term "fasted state" means that the human or other mammal has not ingested 500 calories or more than 500 calories for at least two hours before taking the lurasidone solid oral dosage form and for at least two hours after taking the lurasidone solid oral dosage form.

As used herein, the term "fed state" refers to a human or other mammal who has eaten within about 30 minutes prior to drug administration. For example, the human or other mammal may have consumed at least 350 calories, or consumed an United States Food and Drug Administration (FDA) standard high fat breakfast (or other meal containing a comparable quantity of fat and calories) within said time period, which is high in both fat (approximately 50% of total calorie content of the meal) and calories (approximately 800-1000 calories) within about 30 minutes prior to drug administration.

The term "food effect" as used herein means food-drug interactions which either decrease or increase the extent of drug absorption. In other words the bioavailability for a drug is altered when administered under fasted state, in comparison to the drug when administered in the fed state. It may refer to a relative difference in one or more of $AUC_\infty$, $AUC_{0-t}$, $C_{max}$, and/or $T_{max}$ of a drug, when said drug or a formulation thereof is administered orally to a human, concomitantly with food or in a fed state as compared to the same values when the same formulation is administered in a fasted state or without food.

In one aspect, the pharmaceutical compositions described herein reduce or eliminate the food effect. As used herein, "reducing the food effect" refers to narrowing the difference in bioavailability, e.g., $AUC_\infty$, $AUC_{0-t}$, $C_{max}$, and/or $T_{max}$, for a drug administered under fasted states in comparison to the drug administered under fed states. In certain aspects, the food effect is eliminated. Thus, upon oral administration of a pharmaceutical composition as described herein, to a mammal in need thereof, there is not a significant adverse food effect. In other words, the difference between a pharmacokinetic parameter measured after oral administration to a mammal with and without food, respectively, is less than 40%, e.g., less than 35%, less than 30%, less than 25%, less than 20%, less than 15%, less than 10 or less than 5%.

In other embodiments, the dose of lurasidone is at the most about 98% w/w, or at the most about 95% w/w, or at the most about 90% w/w, or at the most about 85% w/w, or at the most about 80% w/w, or at the most about 75% w/w, or at the most about 70% w/w, or at the most about 65% w/w, or at the most about 60% w/w, or at the most about 55% w/w or at the most about 50% w/w of the dose of the lurasidone administered in the form of a commercially available product.

Pharmacokinetic parameters for the compositions can be measured in a single or multiple dose study using a replicate or a nonreplicate design. For example, the pharmacokinetic parameters can be measured in a single dose pharmacokinetic study using a two-period, two-sequence crossover design. Alternately, a four-period, replicate design crossover study may also be used. Pharmacokinetic parameters characterizing rate and extent of lurasidone absorption are evaluated statistically. The area under the plasma concentration-time curve from time zero to the time of measurement of the last quantifiable concentration ($AUC_{0-t}$) and to infinity ($AUC_{0-infinity}$), $C_{max}$, and $T_{max}$ can be determined according to standard techniques. Statistical analysis of pharmacokinetic data is performed on logarithmic transformed data (e.g., $AUC_{0-t}$, $AUC_{0-infinity}$, or $C_{max}$ data) using analysis of variance (ANOVA).

The difference in AUC of the compositions of the present invention, when administered in the fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

The difference in $C_{max}$ of the compositions of the present invention, when administered in fed versus the fasted state, preferably is less than about 100%, less than about 90%, less than about 80%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, or less than about 3%.

In some aspects, following administration of the pharmaceutical composition to subjects (e.g., fed subjects or fasted subjects), the mean bioavailability is greater than about 20% (e.g., greater than 25%, 30%, 35%, 40%, 45%, 50%, 55%, 60%, 65%, 70%, 75%, 80%, 85%, 90%, 95%, or even 99%) or between about 20% to about 90% (e.g., from 20% to 30%, from 20% to 40%, from 20% to 50%, from 20% to 60%, from 20% to 70%, from 20% to 80%, from 20% to 90%, from 30% to 40%, from 30% to 50%, from 30% to 60%, from 30% to 70%, from 30% to 80%, from 30% to 90%, from 40% to 50%, from 40% to 60%, from 40% to 70%, from 40% to 80%, from 40% to 90%, from 50% to 60%, from 50% to 70%, from 50% to 80%, from 50% to 90%, from 60% to 70%, from 60% to 80%, from 60% to 90%, from 70% to 80%, from 70% to 90%, and from 80% to 90%).

In some aspects, the ratio of the mean bioavailability for fed subjects to the mean bioavailability for fasted subjects is from about 1.0 to about 2.0 (e.g., from 1.0 to 1.1, from 1.0 to 1.2, from 1.0 to 1.3, from 1.0 to 1.4, from 1.0 to 1.5, from 1.0 to 1.6, from 1.0 to 1.7, from 1.0 to 1.8, from 1.0 to 1.9, from 1.3 to 1.4, from 1.3 to 1.5, from 1.3 to 1.6, from 1.3 to 1.7, from 1.3 to 1.8, from 1.3 to 1.9, from 1.3 to 2.0, from 1.5 to 1.6, from 1.5 to 1.7, from 1.5 to 1.8, from 1.5 to 1.9, from 1.5 to 2.0, from 1.7 to 1.8, from 1.7 to 1.9, from 1.7 to 2.0, from 1.8 to 1.9, and from 1.8 to 2.0).

In some aspects, administration of the pharmaceutical composition to fed and fasted subjects produces a coefficient of variation in $AUC_{0-t}$, $T_{max}$, $C_{max}$ and/or $AUC_\infty$ of less than about 60% (e.g., less than 55%, 50%, 45%, 40%, 35%, 30%, 25%, 20%, and 15%). In particular embodiments, the coefficient of variation in $C_{max}$ and/or $AUC_\infty$ is of from about 20% to about 60% (e.g., from 20% to 30%, from 20% to 35%, from 20% to 40%, from 20% to 45%, from 20% to 50%, from 20% to 55%, from 30% to 35%, from 30% to 40%, from 30% to 45%, from 30% to 50%, from 30% to 55%, from 30% to 60%, from 35% to 40%, from 35% to 45%, from 35% to 50%, from 35% to 55%, from 35% to 60%, from 40% to 45%, from 40% to 50%, from 40% to 55%, from 40% to 60%, from 45% to 50%, from 45% to 55%, from 45% to 60%, from 50% to 55%, from 50% to 60%, and from 55% to 60%).

In some aspects, administration of the pharmaceutical composition to a fasted subject produces mean $C_{max}$ that is greater than about 50 ng/mL (e.g., greater than about 60 ng/mL, 70 ng/mL, 80 ng/mL, 90 ng/mL, 100 ng/mL, 110 ng/mL, 120 ng/mL, 130 ng/mL, 140 ng/mL, 150 ng/mL, 200 ng/mL, 250 ng/mL, and/or up to about 300 ng/mL) for a 40 mg eq. dose of lurasidone hydrochloride.

In some aspects, administration of the pharmaceutical composition to a fasted subject produces mean $AUC_{0-\infty}$ that is greater than about 200 hr*ng/mL (e.g., greater than 250 hr*ng/mL, 300 hr*ng/mL, 350 hr*ng/mL, 400 hr*ng/mL, 450 hr*ng/mL, 500 hr*ng/mL, 550 hr*ng/mL and/or greater than about 600 hr*ng/mL) for a 40 mg eq. dose of lurasidone hydrochloride.

Methods for Making Solid Dispersions

The present application relates to pharmaceutical compositions comprising lurasidone solid dispersion and pharmaceutically acceptable excipients. In an embodiment, lurasidone solid dispersion of the present application comprises lurasidone and a pharmaceutically acceptable polymer. In an embodiment, lurasidone solid dispersion of the present application comprises crystalline or amorphous forms of lurasidone free base or lurasidone hydrochloride and a pharmaceutically acceptable polymer.

The solid dispersion composition comprising lurasidone may be formed by any conventional technique, e.g., spray drying, co-grinding, hot melt extrusion, freeze drying, rotary evaporation, solvent evaporation, co-precipitation, lyophilization, or any suitable solvent removal process.

The solid dispersions consist of two or more components, generally a pharmaceutically acceptable carrier (e.g., a polymer), and drug. Optionally, other pharmaceutically acceptable excipients may be included, such as a solubilizer, a surfactant and/or other additives. While not wishing to be bound by theory, the pharmaceutically acceptable carrier in the solid dispersion may reduce the molecular mobility of the drug to avoid the phase separation and re-crystallization of drug during storage. Thus, the resulting solid dispersions may have increased solubility. In certain aspects, the increase in solubility of the drug in solid dispersion is mainly because drug remains in amorphous form which is associated with a higher energy state as compared to crystalline counterpart and due to that it requires very less external energy to dissolve.

In some embodiments, at least about 90% (e.g., at least 95%, 96%, 97%, 98%, 99%, 99.5%, or even 99.9%, such as from 90% to 99.9%, from 90% to 99.5%, from 90% to 99%, from 90% to 98%, from 90% to 97%, from 90% to 96%, from 90% to 95%, from 95% to 99.9%, from 95% to 99.5%, from 95% to 99%, from 95% to 98%, from 95% to 97%, and from 95% to 96%) of the lurasidone is in amorphous form.

In an embodiment, lurasidone solid dispersion of the present application comprises lurasidone and a pharmaceutically acceptable polymer, wherein the pharmaceutically acceptable polymer is selected from the group consisting of hydroxypropyl methyl cellulose acetate succinate (HPMC-AS), polyvinyl pyrrolidine vinyl acetate (PVP/VA) copolymer, hydroxypropyl methylcellulose phthalate (HPMCP) and polyvinyl caprolactam-polyvinyl acetate-polyethylene glycol graft copolymer (PCL-PVAc-PEG).

In some aspects, the pharmaceutical composition includes a solid dispersion of the lurasidone or a pharmaceutically acceptable salt thereof, and a pharmaceutically acceptable carrier (e.g., a pharmaceutically acceptable polymer), where the weight ratio of the lurasidone or a pharmaceutically acceptable salt thereof, to the pharmaceutically acceptable carrier is from about 1:6 to about 1:1.5 (e.g., from 1:6 to 1:2, from 1:6 to 1:2.5, from 1:6 to 1:3, from 1:6 to 1:3.5, from 1:6 to 1:4, from 1:6 to 1:4.5, from 1:6 to 1:5, from 1:5 to 1:2, from 1:5 to 1:2.5, from 1:5 to 1:3, from 1:5 to 1:3.5, from 1:5 to 1:4, from 1:5 to 1:4.5, from 1:5 to 1:1.5, from 1:4 to 1:1.5, from 1:4 to 1:2, from 1:4 to 1:2.5, from 1:4 to 1:3, from 1:4 to 1:3.5, from 1:3 to 1:1.5, from 1:3 to 1:2, from 1:3 to 1:2.5, and from 1:2 to 1:1.5).

In an embodiment, a lurasidone solid dispersion of the present application comprises lurasidone and a pharmaceutically acceptable polymer, wherein lurasidone and polymer are in the ratio of about 1:1 to about 1:4 (w/w).

In an embodiment, a lurasidone solid dispersion of the present application comprises lurasidone and a pharmaceutically acceptable polymer, wherein lurasidone is lurasidone free base and the polymer is HPMC-AS. More specifically, lurasidone free base and HPMC-AS are in the ratio of about 1:1 to about 1:4 (w/w), preferably in the ratio of about 1:3 (w/w).

In an embodiment, a lurasidone solid dispersion of the present application comprises lurasidone and a pharmaceutically acceptable polymer, wherein lurasidone is lurasidone free base and the polymer is PVP/VA copolymer. More specifically, lurasidone free base and PVP/VA are in the ratio of about 1:1 to about 1:4 (w/w), preferably in the ratio of about 1:3 (w/w).

In an embodiment, a lurasidone solid dispersion of the present application comprises lurasidone and a pharmaceutically acceptable polymer, wherein lurasidone is lurasidone free base and the polymer is HPMCP. More specifically, lurasidone free base and HPMCP are in the ratio of about 1:1 to about 1:4 (w/w), preferably in the ratio of about 1:3 (w/w).

In an embodiment, a lurasidone solid dispersion of the present application comprises lurasidone and a pharmaceutically acceptable polymer, wherein lurasidone is lurasidone free base and the polymer mixture which is a mixture of HPMC-AS and PVP/VA in the ratio of 1:1. More specifically, lurasidone free base and HPMC-AS and PVP/VA polymer mixture are in the ratio of about 1:1 to about 1:4 (w/w), preferably in the ratio of about 1:3 (w/w).

The solid dispersions of the present invention may include one or more solubilizers, i.e., additives which increase solubility of the pharmaceutical active ingredient in the solid dispersion or additives which act as pore-forming agents in the solid dispersion. Suitable solubilizers for use in compositions of the present invention include sorbitol, mannitol, transcutol, polyvinylalcohol, hydroxypropyl methylcellulose, hydroxypropyl cellulose, polyvinylpyrrolidone, glycofurol and transcutol. The concentration of solubilizer ranges from about 1% to about 30% w/w of polymer concentration.

The solid dispersions of the present invention optionally may include one or more surfactants. Surfactants are compounds which are capable of improving the wetting of the drug and/or enhancing the dissolution. The surfactants can be selected from hydrophilic surfactants or lipophilic surfactants or mixtures thereof. The surfactants can be anionic, nonionic, cationic, and zwitterionic surfactants. Surfactants according to the present invention include, but not limited to, polyoxyethylene alkylaryl ethers such as polyoxyethylene lauryl ether, polyoxyethylene cetyl ether, polyoxyethylene stearyl ether; polyethylene glycol fatty acid esters such as PEG monolaurate, PEG dilaurate, PEG distearate, PEG dioleate; polyoxyethylene sorbitan fatty acid ester such as polysorbate 40, polysorbate 60, polysorbate 80; sorbitan fatty acid mono esters such as sorbitan monolaurate, sorbitan monooleate, sorbitan sesquioleate, sorbitan trioleate, sodium lauryl sulfate, sodium dioctyl sulfosuccinate (DOSS), lecithin, stearylic alcohol, cetostearylic alcohol, cholesterol, polyoxyethylene ricin oil, polyoxyethylene fatty acid glycerides, cremophor RH 40, and the like or combinations thereof. The concentration of surfactant ranges from about 1% to about 10% w/w of polymer concentration.

The lurasidone starting material used in the process for preparation of the solid dispersion may be in any crystalline form or amorphous form. Alternatively, it may be obtained in situ from a previous processing step.

The lurasidone in the solid dispersion obtained may be present in either crystalline or amorphous powder form.

In some aspects herein, the percentage loading of lurasidone in the solid dispersion is from about 1% to about 90% (w/w) (e.g., from 1% to 19%, from 10% to 19%, from 10% to 20%, from 10% to 30%, from 10% to 40%, from 10% to 50%, from 10% to 60%, from 10% to 70%, from 10% to 80%, from 10% to 90%, from 20% to 30%, from 20% to 40%, from 20% to 50%, from 20% to 60%, from 20% to 70%, from 20% to 80%, from 20% to 90%, from 21% to 30%, from 21% to 34%, from 21% to 40%, from 21% to 50%, from 21% to 60%, from 21% to 70%, from 21% to 80%, from 21% to 90%, from 30% to 40%, from 30% to 50%, from 30% to 60%, from 30% to 70%, from 30% to 80%, from 30% to 90%, from 36% to 40%, from 36% to 49%, from 36% to 60%, from 36% to 70%, from 36% to 80%, from 36% to 90%, from 40% to 50%, from 40% to 60%, from 40% to 70%, from 40% to 80%, from 40% to 90%, from 50% to 60%, from 50% to 70%, from 50% to 80%, from 50% to 90%, 51% to 60%, from 51% to 70%, from 51% to 80%, from 51% to 90%, from 60% to 70%, from 60% to 80%, from 60% to 90%, from 70% to 80%, and from 70% to 90%). In some preferred embodiments, the percentage loading of lurasidone is from about 10% to about 60% (w/w) (e.g., from 10% to 20%, from 10% to 30%, from 10% to 40%, from 10% to 50%, from 10% to 60%, from 20% to 30%, from 20% to 40%, from 20% to 50%, from 20% to 60%, from 30% to 40%, from 30% to 50%, from 30% to 60%, from 40% to 50%, and from 40% to 60%).

In an aspect, methods are provided for preparing a pharmaceutical composition as described herein, which comprise preparing a mixture (e.g., a liquid mixture) or a solution including lurasidone or a pharmaceutically acceptable salt thereof, and a pharmaceutically acceptable carrier (e.g., a matrix polymer); and spray drying the mixture or the solution to form a solid dispersion (e.g., a spray dried dispersion).

In an aspect, methods are provided for preparing a pharmaceutical composition as described herein, which comprise preparing a mixture of lurasidone or a pharmaceutically acceptable salt thereof, and a pharmaceutically acceptable carrier; heating (e.g., up to or above the transition glass temperature or melting temperature of the matrix polymer) the mixture to form a homogenous molten mass; extruding the molten mass; and cooling the molten mass to form a solid dispersion (e.g., a hot melt extrusion).

The resultant solid dispersions can be blended with one or more excipients, as described herein, and then granulated and/or compacted to produce a final blend for encapsulating or tableting. In particular embodiments, the solid dispersion may be combined with one or more excipient(s) may be included to form granules, e.g., such as a binding agent, a filler, a disintegrating agent, a wetting agent, a glidant, and a lubricant.

Spray Drying Process

In certain aspects, the solid dispersions are made by spray drying. Generally, one or more pharmaceutically acceptable carrier(s) and lurasidone are combined either with or without solvent(s) to form a mixture or a solution, which can be spray-dried to form a solid dispersion. For example, in a typical spray drying technique, the solid dispersion is formed by dispersing or dissolving the drug and a polymer in a suitable solvent, and subsequently spray drying to form the solid dispersion in the form of a powder.

Any suitable solvent may be used for spray drying. Examples of suitable solvents or dispersion media include but are not limited to: methylene chloride, chloroform, ethanol, methanol, propan-2-ol, ethyl acetate, acetone, water, or mixtures thereof.

In certain aspects, the solution may have about 4% (w/w) to about 15% (w/w) of total solids. Percentage (w/w) total solids is determined by dividing the total mass of the compound and one or more matrix polymers by the total mass of the compound, one or more matrix polymers, and one or more solvents.

In particular embodiments, the SDD includes about 20% (w/w) of lurasidone, with the one or more pharmaceutically acceptable carrier(s), such as matrix polymers. Preferably, the weight ratio of lurasidone to the one or more pharmaceutically acceptable carrier(s) is about 1:4.

For example, to produce a 20% (w/w) lurasidone in a SDD, a solution was prepared having about 2% (w/w) lurasidone and about 8% (w/w) of a pharmaceutically acceptable matrix polymer or a combination of a pharmaceutically acceptable matrix polymer in acetone. The solution was then spray dried at the appropriate temperature (e.g., between about 95° C. and 110° C. for HPMC-AS at the appropriate solution flow rate).

The solution can be spray dried to form a spray-dried dispersion (SDD), which can optionally be further subjected to suitable drying steps. Optionally, other excipients may then be blended into the resulting solid dispersions (with or without milling or grinding) to form a composition suitable for use in dosage forms such as tablets and capsules.

Hot Melt Extrusion Process

In certain aspects, the solid dispersions are made by hot melt extrusion ("HME"), e.g., a process whereby a composition is heated and/or compressed to a molten (or softened) state and subsequently forced through an orifice in a die where the extruded product is formed into its final shape in which it solidifies upon cooling. Hot melt extrusion is simple and easy to operate, and decreases energy consumption, and increases productivity.

In the HME process, a blend is conveyed through one or more heating zones typically by a screw mechanism. The screw or screws are rotated by a variable speed motor inside a cylindrical barrel where only a small gap exists between the outside diameter of the screw and the inside diameter of the barrel. In this conformation, high shear is created at the barrel wall and between the screw fights by which the various components of the powder blend are well mixed and disaggregated. The die can be a dual manifold, multi-manifold or feed-block style die. As used herein, the term extrudate refers to hot-melt extruded composition.

In an embodiment, lurasidone solid dispersion of the present application is obtained by hot melt extrusion. A physical mixture of lurasidone base and polymer was subjected to hot melt extrusion at 70-180° C. through a hot melt extruder (such as omicron 10P) having the same direction rotation type twin screws. The obtained hot-melt extrusion product was chilled, milled and passed through a 30-mesh screen.

In other embodiments, the mixture can then be fed into a pre-heated extruder (e.g., an extruder having temperature zones between about 70° C. to about 180° C.) to produce an initial extrudate.

Preferably, the hot-melt extrusion is to be carried out at a temperature that allows the dissolution of the lurasidone used as staring material within the mixture of pharmaceutically acceptable excipients, e.g., an enteric polymer and/or a non-enteric polymer. In certain embodiments, the pharmaceutically acceptable carrier(s) and lurasidone can be heated near or past the glass transition temperature Tg or melting temperature Tm to form a liquid mixture. After the mixture is heated to form a homogenous molten mass, it may be extruded and cooled to form a solid dispersion.

The temperature and screw speed of the hot melt extruder are selected based on the type of pharmaceutically acceptable carrier employed, e.g., to extrude the target mixture smoothly, wherein the extrusion speed and the yield can meet the requirements, and the solubilization effect is good.

In certain aspects, optionally, a surfactant or solubilizer may also be included in the mixture to enhance dissolution and/or enhance stability. An exemplary surfactant includes sodium lauryl sulfate, in any useful or effective amount (e.g., from about 1% to about 10% (w/w), e.g., about 5% (w/w)).

The extrudates can optionally be pelletized or milled to form a solid dispersion amenable for further processing in a suitable unit dosage form. In certain aspects, the extrudate is then pelletized and milled (e.g., to a size less than about 500 µm) to produce a milled extrudate. The milled/pelletized extrudate can be sieved and blended with various pharmaceutically acceptable excipients, where the resultant blend was then co-milled. The co-milled blend can be further processed by adding a lubricant (e.g., magnesium stearate), and the resultant, processed blend can be used to fill a unit dosage form (e.g., capsule).

Pharmaceutical Compositions Comprising Lurasidone Solid Dispersions

The solid dispersion may be used for filling any one of the unit dosage forms described herein (e.g., a capsule) or for tableting. The solid dispersion can optionally be further processed before filling or tableting. Exemplary further processing includes spheronizing, pelletizing, milling, injection molding, sieving, and/or calendering the solid dispersion.

Amorphous solid dispersions of lurasidone of the present application can be optionally subjected to a particle size reduction procedure before or after the completion of drying of the product to produce desired particle sizes and distributions. Milling or micronization can be performed to achieve the desired particle sizes or distributions. Equipment that may be used for particle size reduction include, without limitation thereto, ball mills, roller mills, hammer mills, and jet mills.

In another general aspect, there is provided amorphous form of lurasidone solid dispersion comprising amorphous form of lurasidone having particle size distributions wherein D90 is less than about 500 microns or less than about 200 microns or less than about 100 microns or less than about 50 microns or less than about 40 microns or less than about 30 microns or less than about 20 microns or less than about 10 microns or any other suitable particle sizes.

The lurasidone solid dispersion may be combined with pharmaceutically acceptable excipients to make other pharmaceutical compositions, or a finished dosage form. The one or more additional pharmaceutically acceptable excipients are selected from diluents, binders, disintegrants, fillers, lubricants, glidants, surfactants, stabilizing agents, antioxidants, alkaline stabilizers, colors, flavors, preservatives, and combinations thereof.

In an embodiment, pharmaceutical compositions comprising lurasidone solid dispersion and pharmaceutically acceptable excipients are prepared by using, but not limited, to wet granulation, dry granulation, and direct compression.

In an embodiment, pharmaceutical compositions comprising lurasidone solid dispersion and pharmaceutically acceptable excipients are prepared by using direct compression, which process comprises mixing lurasidone solid dispersion and pharmaceutically acceptable excipients, the resultant mixture is either compressed to tablet or filled in hard gelatin capsules.

In an embodiment, pharmaceutical compositions comprising lurasidone solid dispersion and pharmaceutically acceptable excipients are prepared by using dry granulation, wherein dry granulation is carried out by either direct compaction or roller compaction or both.

In an embodiment, pharmaceutical compositions comprising lurasidone solid dispersion and pharmaceutically acceptable excipients are prepared by using direct compaction dry granulation, which process comprises compressing mixture of lurasidone solid dispersion and intragranular material into slug, compressed slugs are milled and passed through mess screen manually or automatically which results in granules. The resulting granules were mixed with extra granular material. This final mixture is either compressed to tablet or filled in hard gelatin capsules.

In an embodiment, pharmaceutical compositions comprising lurasidone solid dispersion and pharmaceutically acceptable excipients are prepared by using roller compaction dry granulation, which process comprises passing a mixture of lurasidone solid dispersion and intragranular material between two high-pressure rollers to form consolidated and densified material, the resultant densified material is then reduced to a uniform granule size by milling, which were then mixed with extra granular material. This final mixture is either compressed to tablet or filled in hard gelatin capsules.

In an embodiment, pharmaceutical compositions comprising lurasidone solid dispersion and pharmaceutically acceptable excipients are prepared by wet granulation, which process comprises: (a) mixing lurasidone solid dispersion and pharmaceutically acceptable excipients (b) adding sufficient solvent, wherein the solvent is selected form water, isopropanol, ethanol, to the mixture obtained from step (a) under shear to generate granules; (c) milling or grinding the granules followed by sieving of said granules; optionally mixing with other excipients. This final mixture is either compressed to tablet or filled in hard gelatin capsules.

The pharmaceutical compositions of the present invention include one or more diluents. In an embodiment, suitable diluents include microcrystalline cellulose, calcium carbonate, calcium phosphate-dibasic, calcium phosphate-tribasic, calcium sulfate, cellulose powdered, dextrates, dextrins, dextrose excipients, fructose, kaolin, lactitol, lactose, mannitol, sorbitol, starch, starch pregelatinized, sucrose, sugar compressible, sugar confectioners and the like.

In an embodiment, diluent is included either in intragranular material or extra granular material or both.

In an embodiment, the concentration of diluent ranges from about 35% to about 60% w/w of total composition.

In an embodiment, the diluent concentration in the intragranular material ranges from about 10% to about 60% w/w of total composition, preferably about 25% to about 35%, more preferably about 27% w/w.

In an embodiment, the diluent concentration in the extra granular material ranges from about 10% to about 60% w/w of total composition, preferably about 25% to about 35%, more preferably about 28% w/w.

In an embodiment, suitable binders include methyl cellulose, hydroxypropyl cellulose, hydroxypropyl methylcellulose, polyvinyl pyrrolidone, microcrystalline cellulose, gelatin, gum arabic, ethyl cellulose, polyvinyl alcohol, pullulan, pregelatinized starch, agar, tragacanth, sodium alginate, propylene glycol and the like.

In an embodiment, the binder concentration ranges from about 10% to about 60% w/w of total composition, preferably about 25% to about 35% w/w.

In an embodiment, suitable disintegrating agents include croscarmellose sodium, low-substituted hydroxypropyl cellulose (L-HPC), sodium starch glycollate, carboxymethyl cellulose, calcium carboxymethyl cellulose, sodium carboxymethyl cellulose, starch, crystalline cellulose, hydroxypropyl starch, pregelatinized starch, and the like and mixtures thereof.

In an embodiment, the disintegrating agent concentration ranges from about 1% to about 10% w/w of total composition.

In an embodiment, suitable lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like and mixtures thereof.

In an embodiment, the lubricants/glidants concentration ranges from about 0.5% to about 5% w/w of total composition.

In an embodiment, suitable coloring agent include dyes and pigments such as iron oxide red or yellow, titanium dioxide, talc.

In an embodiment, the coloring agent concentration ranges from about 0.1% to about 1% w/w of total composition.

Solid dispersion technique is useful in improving bioavailability by increasing solubility. There are various methods which are used for preparing a solid dispersion like solvent evaporation method, melting method and spray drying method. Conversion of crystalline form of pharmaceutical active ingredient to amorphous form when formulated into a solid dispersion is one of the mechanisms responsible for improved solubility, which in turn improves bioavailability of formulation, and reduces the effect of food on dissolution of lurasidone.

In an embodiment, solid dispersion and tablets manufactured as per the present invention were tested for comparative dissolution by using USP apparatus-II (paddle) in 0.1N HCl followed by pH 6.8 phosphate buffer and McIlvaine buffer at pH 3.8 followed by pH 6.8.

In an embodiment, tablets manufactured as per the present invention were tested for comparative dissolution by using USP apparatus-II (paddle) in 0.01N HCl followed by FaSSIF media at pH 6.5.

In an embodiment, tablets manufactured as per the present invention were tested for comparative dissolution by using USP apparatus-II (paddle) in 0.01N HCl followed by FeSSIF media at pH 5.0.

In an embodiment, tablets manufactured as per the present invention were tested for comparative dissolution by using USP apparatus-II (paddle) in McIlvaine buffer at pH 6.5.

In an embodiment, tablets manufactured as per the present invention were tested for comparative dissolution by using USP apparatus-II (paddle) in FaSSIF media at pH 6.5.

In an embodiment, tablets manufactured as per the present invention were tested for comparative dissolution by using USP apparatus-II (paddle) in 0.1N HCl.

In an embodiment, tablets manufactured as per the present invention were tested for comparative dissolution by using USP apparatus-II (paddle) in acetate buffer at pH 4.5.

The 0.1N HCl acid dissolution media was prepared by adding 68 mL of concentrated hydrochloric acid to 8000 mL of water and mixing well. 675 mL of resultant solution was used as acid media. Buffer media was obtained by adding 225 mL of pH 6.8 phosphate-citrate buffer to the 675 mL of acid media obtained above, mixed well and adjusted pH to 6.8 by using the 2N sodium hydroxide solution or hydrochloric acid.

McIlvaine buffer acid media was prepared by mixing 600 mL of citric acid buffer (0.025 molar) and 400 mL of disodium hydrogen phosphate buffer (0.05 molar), adjust the pH to 3.8 by using diluted ortho-phosphoric acid. 675 mL of the resultant solution was used as McIlvaine buffer acid media at pH 3.8. Buffer media at pH 6.8 was prepared by adding 225 mL of pH 6.8 phosphate-citrate buffer to 675 mL of McIlvaine buffer acid media and adjusting pH to 6.8 with 2N NaOH or ortho-phosphoric acid.

In an embodiment, the present application relates to methods of using pharmaceutical compositions of the present application for treatment of schizophrenia, bipolar disorders or senile dementia.

The requirement of improved and/or more flexible compositions may be to obtain the same or better bioavailability than already seen from the commercially available products.

In an embodiment, the present application provides a method of treating CNS disorder in human, which method comprises administering to the human in a fasted state, an oral dosage form comprising an amount of lurasidone effective to treat said CNS disorder, wherein the area under the plasma concentration versus time curve ($AUC_{0-inf}$) of the lurasidone in the human subsequent to said administering is from 70% to 143% of the mean area under the lurasidone plasma concentration versus time curve ($AUC_{0-inf}$) resulting from administration of a control lurasidone immediate release oral tablet containing the same amount of lurasidone to a cohort of humans in a fed state.

Dosage and Administration

The pharmaceutical compositions as described herein may be used in methods of treatment, in which an effective amount of lurasidone or a pharmaceutically acceptable salt thereof is administered to a patient. The pharmaceutical compositions described herein may be used to treat various CNS disorders, including but not limited to depression or depressive episodes associated with biopolar I disorder (bipolar depression) in adults and pediatric patients, schizophrenia and/or senile dementia. Senile dementia includes both Alzheimer's dementia and cerebrovascular dementia. In certain aspects, the pharmaceutical compositions described herein may be used to treat adults and adolescents (e.g., about 13-17 years). In certain aspects, the pharmaceutical compositions described herein may be used as monotherapy or as adjunctive therapy. For example, for treating bipolar depression, the pharmaceutical compositions described herein may be used in adjunctive therapy with lithium or valproate. In certain aspects, examples of conditions that may be treated or prevented by administering pharmaceutical compositions as described herein include CNS or mental diseases, e.g., schizophrenia, bipolar I disorder, autism, bipolar disorder and depression.

For administration to animal or human subjects, the pharmaceutical compositions comprise an effective dosage amount of lurasidone or a pharmaceutically acceptable salt thereof. The formulation may be prepared using conventional methods, for example, depending on the subject to be treated, the mode of administration, and the type of treatment desired (e.g., prevention, prophylaxis, or therapy).

The lurasidone or pharmaceutically acceptable salt thereof, may be present in amounts totaling 1-95% by weight of the total weight of the composition.

Preferably, the pharmaceutical composition will be provided in a dosage form that is suitable for oral administration, including but not limited to hard capsules (e.g., hard gelatin capsules or hard hydroxypropyl methylcellulose capsules), soft gelatin capsules, tablets, caplets, enteric coated tablets, chewable tablets, enteric coated hard gelatin capsules, enteric coated soft gelatin capsules, minicapsules, lozenges, films, strips, gelcaps, dragees, suspensions, syrups, or sprinkles. The compositions may be formulated according to conventional pharmaceutical practice.

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

In an aspect, the invention relates to a pharmaceutical composition in unit dosage form for oral administration, the composition including from about 20 mg to about 160 mg (e.g., from 20 mg to 30 mg, from 20 mg to 40 mg, from 20 mg to 50 mg, from 20 mg to 75 mg, from 20 mg to 100 mg, from 20 mg to 125 mg, from 20 mg to 160 mg, from 30 mg to 40 mg, from 30 mg to 50 mg, from 30 mg to 75 mg, from 30 mg to 100 mg, from 30 mg to 125 mg, from 30 mg to 160 mg, from 40 mg to 50 mg, from 40 mg to 75 mg, from 40 mg to 100 mg, from 40 mg to 125 mg, from 40 mg to 160 mg, from 50 mg to 75 mg, from 50 mg to 100 mg, from 50 mg to 125 mg, from 50 mg to 160 mg, from 60 mg to 75 mg, from 60 mg to 100 mg, from 60 mg to 125 mg, from 60 mg to 160 mg, from 70 mg to 75 mg, from 70 mg to 100 mg, from 70 mg to 125 mg, from 70 mg to 160 mg, from 80 mg to 100 mg, from 80 mg to 125 mg, from 80 mg to 160 mg, from 90 mg to 100 mg, from 90 mg to 125 mg, from 90 mg to 160 mg, from 100 mg to 125 mg, or from 100 mg to 160 mg) of lurasidone, or a pharmaceutically acceptable salt thereof (e.g., lurasidone hydrochloride). Preferred dosage amounts include 20 mg, 40 mg, 60 mg, 80 mg, or 120 mg of lurasidone hydrochloride, or 18.62 mg, 37.24 mg, 55.87 mg, 74.49 mg or 111.74 mg of lurasidone free base.

In an aspect, the invention relates to certain methods of treatment comprising administration of a pharmaceutical composition described herein, where the total daily dosage amount is from about 20 mg to about 160 mg (e.g., from 20 mg to 30 mg, from 20 mg to 40 mg, from 20 mg to 50 mg, from 20 mg to 75 mg, from 20 mg to 100 mg, from 20 mg to 125 mg, from 20 mg to 160 mg, from 30 mg to 40 mg, from 30 mg to 50 mg, from 30 mg to 75 mg, from 30 mg to 100 mg, from 30 mg to 125 mg, from 30 mg to 160 mg, from 40 mg to 50 mg, from 40 mg to 75 mg, from 40 mg to 100 mg, from 40 mg to 125 mg, from 40 mg to 160 mg, 50 mg to 75 mg, from 50 mg to 100 mg, from 50 mg to 125 mg, from 50 mg to 160 mg, from 60 mg to 75 mg, from 60 mg to 100 mg, from 60 mg to 125 mg, from 60 mg to 160 mg, from 70 mg to 75 mg, from 70 mg to 100 mg, from 70 mg to 125 mg, from 70 mg to 160 mg, from 80 mg to 100 mg, from 80 mg to 125 mg, from 80 mg to 160 mg, from 90 mg to 100 mg, from 90 mg to 125 mg, from 90 mg to 160 mg, from 100 mg to 125 mg or from 100 mg to 160 mg) of lurasidone, or a pharmaceutically acceptable salt thereof (e.g., lurasidone hydrochloride). Preferred dosage amounts include 20 mg, 40 mg, 60 mg, 80 mg, or 120 mg of lurasidone hydrochloride, or 18.62 mg, 37.24 mg, 55.87 mg, 74.49 mg or 111.74 mg of lurasidone free base.

The term "unit dosage form" refers to a physically discrete unit suitable as a unitary dosage, such as a tablet, caplet, hard capsule, or soft capsule, each unit containing a predetermined quantity of a drug.

By "effective" amount is meant the amount of a drug sufficient to treat, prevent, or ameliorate a condition in a subject or patient. The effective amount of lurasidone or pharmaceutically acceptable salt thereof, used to practice the present invention for therapeutic management of a condition may be determined and adjusted by a person of ordinary skill to provide the appropriate amount and dosage regimen, e.g., depending upon one or more of the manner of administration, the age, body weight, sex, and/or general health of the patient.

As used herein, "to treat" a condition or "treatment" of the condition is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

EXAMPLES

The following examples are exemplary and not intended to be limiting. The above disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

In the following examples, the following preparations were used, and prepared by the general methods described below:

(i) Preparation of 0.01N HCl acid media: 68 mL of concentrated hydrochloric acid was added to 8000 mL of water and mixed well.

(ii) Preparation of 0.01N HCl media: 8.5 mL of concentrated hydrochloric acid was added to 1000 mL of water and mixed well.

(iii) Preparation of pH 4.5 acetate buffer: 3.0 g of sodium acetate trihydrate was dissolved in 1000 mL of water, and the pH was adjusted with q.s. glacial acetic acid to a pH of 4.5±0.05.

(iv) Preparation of McIlvaine buffer of pH 6.5 with 0.1% Tween 80: 204.8 g of disodium hydrogen phosphate anhydrous and 52.8 g of citric acid anhydrous were dissolved in 10,000 mL of water, and the pH was adjusted with q.s. ortho-phosphoric acid to a pH of 6.50±0.05. Then, 10 g of Tween 80 was added to the above solution and stirred until dissolved completely.

(v) Preparation of FaSSIF (Fasted state simulated intestinal fluid) stock solution: 2.53 g sodium hydroxide, 23.7 g sodium dihydrogen phosphate monohydrate, and 37.1 g sodium chloride were added to 3 L of water and mixed thoroughly. The pH was adjusted to a pH of 6.50±0.05 with q.s. sodium hydroxide or q.s. hydrochloric acid. Then, 13.6 g FaSSIF powder was added to the above solution.

(vi) Preparation of FeSSIF (Fed state simulated intestinal fluid) stock solution: 20.2 g sodium hydroxide, 43.3 g glacial acetic acid, and 59.4 g sodium chloride were added to 2.5 L of water and mixed thoroughly. The pH was adjusted to a pH of 5.0±0.05 with q.s. sodium hydroxide or q.s. acetic acid. Then, 56.0 g FaSSIF powder was added to the above solution.

Example 1: Composition of Lurasidone

A lurasidone film-coated tablet was prepared, having the composition set forth in Table 1.

TABLE 1

| Composition 1 | |
|---|---|
| Components | (mg/unit) |
| Granules of extrudate 1 | |
| Lurasidone | 29.79 |
| Hypromellose acetate succinate (HPMC-AS) | 89.37 |

TABLE 1-continued

Composition 1

| Components | (mg/unit) |
|---|---|
| Granules of extrudate 2 | |
| Lurasidone | 7.45 |
| Kollidon ® VA 64 (PVP/VA) | 22.35 |
| Total weight of granules of extrudate 1 and extrudate 2 | 148.95 |
| Extra-granular material | |
| Microcrystalline cellulose (Avicel PH102) | 139.04 |
| Croscarmellose sodium (Ac-Di-Sol) | 9 |
| Aerosil | 1.5 |
| Magnesium stearate | 1.5 |
| Total weight | 300 |
| OPADRY ® II white | 9 |
| Weight of film coated tablet | 309 |

Manufacturing Procedure:

Preparation of granules of extrudate 1: The lurasidone and HPMC-AS were sifted together through a 25-mesh screen. The co-sifted material was loaded into a blender and blended for 30 minutes at 10 rpm to obtain a premix blend. The premix blend was extruded in a hot melt extruder (Omicron 10P). The obtained extrude 1 was milled and passed through a 60-mesh screen to provide granules of extrudate 1. FIG. 1 illustrates the Powder X-Ray Diffraction (PXRD) pattern of the solid dispersion composition corresponding to extrudate 1 in composition 1.

Figure 2:
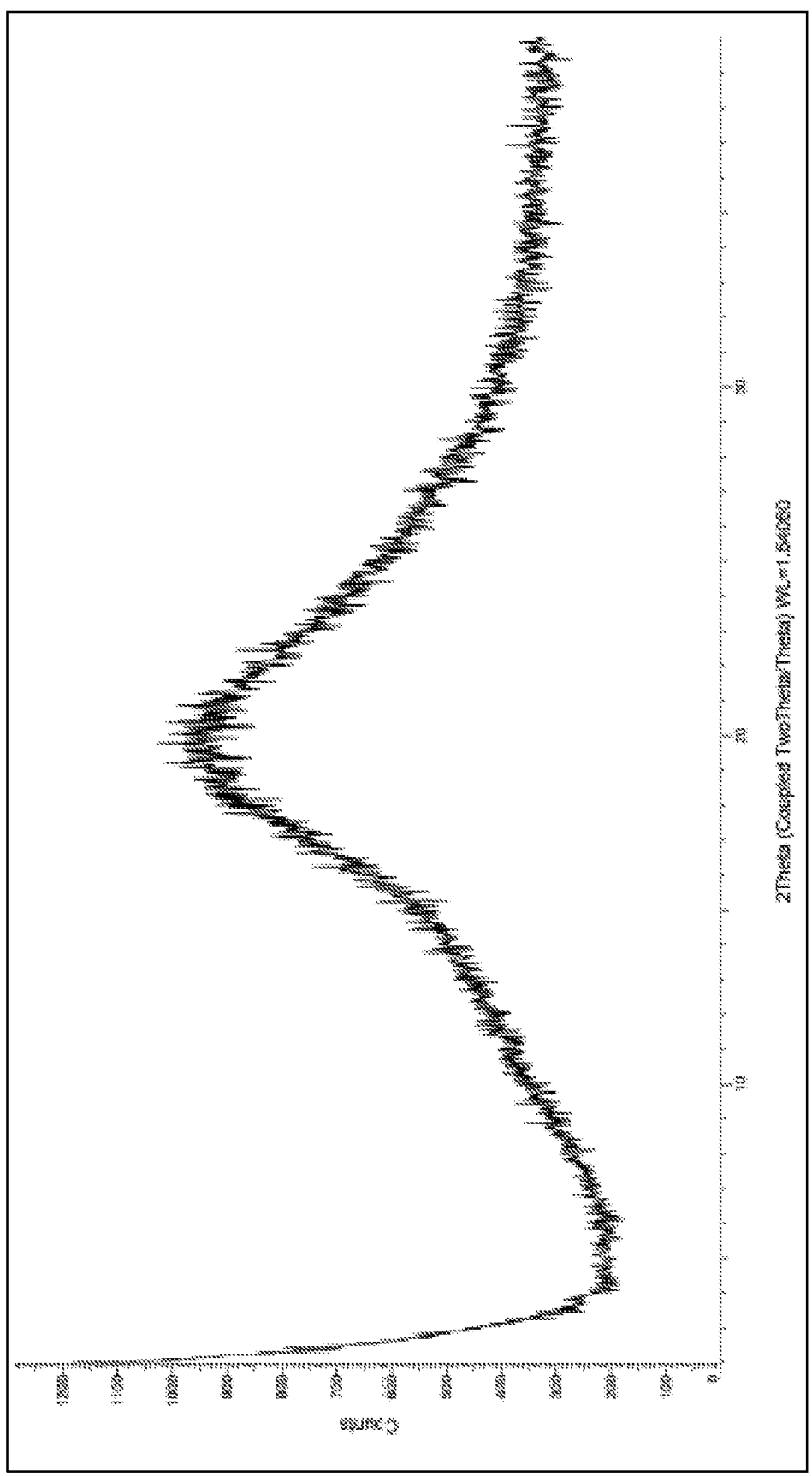
FIG. 2 is the PXRD pattern of the solid dispersion composition corresponding to extrudate 2 in Composition 1 (in Example 1).

Preparation of granules of extrudate 2: The lurasidone and PVP/VA were sifted through a 25-mesh screen. Then, the co-sifted material was loaded into a blender and blended for 30 minutes at 10 rpm to obtain a premix blend. The premix blend was extruded in a hot melt extruder. The obtained extrude 1 was milled and passed through a 60-mesh screen to provide granules of extrudate 2. FIG. 2 illustrates the Powder X-Ray Diffraction (PXRD) pattern of the solid dispersion composition corresponding to extrudate 2 in composition 1.

Extra-granular material: Microcrystalline cellulose, croscarmellose sodium and Aerosil were passed through a 40-mesh screen and added to a blender. Granules of extrudates 1 and 2 were added to the blender and blended for 10 minutes at 10 rpm to obtain a pre-lubricated blend. Magnesium stearate was sifted through a 60-mesh screen and added to the pre-lubricated blend in the blender, followed by blending for 5 minutes at 10 rpm to obtain a lubricated blend. The lubricated blend was compressed into tablets. The tablets were coated with OPADRY® II white 85F18422 aqueous dispersion.

Hot melt extrusion to prepare the granules of extrudate 1 and extrudate 2 in the above manufacturing procedure was carried out using an Omicron 10P extruder. The process parameters maintained during the hot melt extrusion process for extrudate 1 and extrudate 2 are given below in Table 2.

TABLE 2

| Process parameter for preparing extrudate 1 & 2 | Range |
|---|---|
| Screw speed | 250-400 rpm |
| Zone1 (Conveying Zone) | 33-35° C. |
| Zone2 (Blending zone) | 70-90° C. |

TABLE 2-continued

| Process parameter for preparing extrudate 1 & 2 | Range |
|---|---|
| Zone3 (Mixing zone) | 120-180° C. |
| Zone4 (Conveying zone) | 120-180° C. |
| Chiller roller temperature | 20° C. |

Example 2

A lurasidone hydrochloride film-coated tablet composition was prepared, having the composition set forth in Table 3.

TABLE 3

Composition 2

| Components | mg/unit |
|---|---|
| Lurasidone Hydrochloride | 40 |
| Hypromellose Acetate Succinate (HPMC-AS) | 120 |
| Intra-granular material | |
| Microcrystalline cellulose (Avicel PH 101) | 110 |
| Colloidal Silicon dioxide (Aerosil 200) | 1.35 |
| Magnesium stearate | 1.35 |
| Extra-granular material | |
| Microcrystalline cellulose (Avicel PH 102) | 113.3 |
| Croscarmellose Sodium (Ac-di-sol) | 12 |
| Magnesium stearate | 2 |
| Coating | |
| OPADRY ® II white | 12 |
| Total | 412 |

Manufacturing Procedure:

Step 1: The lurasidone HCl was added to methylene chloride in a container, and stirred until a clear solution was obtained. HPMC-AS and isopropyl alcohol (IPA) were added to the obtained solution, and stirred until a clear solution was obtained.

Figure 3:
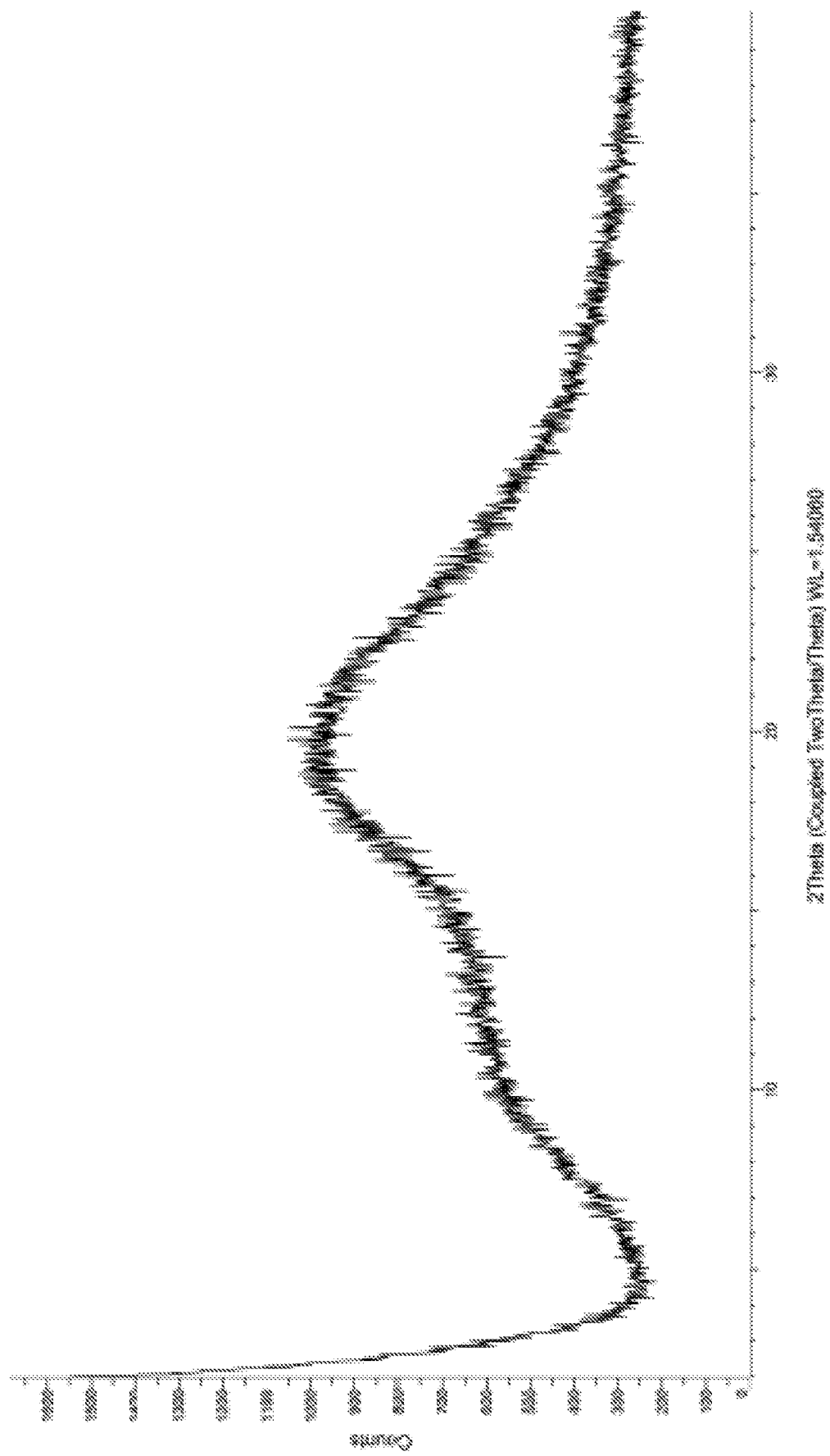
FIG. 3 shows the Powder X-Ray Diffraction (PXRD) pattern of the lurasidone solid dispersion in composition 2 (in Example 2).

Step 2: The solution from step 1 was spray dried using a spray dryer to obtain a lurasidone solid dispersion. The spray drying process parameters are provided in Table 4A. FIG. 3 shows the Powder X-Ray Diffraction (PXRD) pattern of the lurasidone solid dispersion in composition 2.

Step 3: The lurasidone solid dispersion (from step 2), microcrystalline cellulose, and Aerosil were passed through a 40-mesh screen, added to a blender and blended for 20 minutes at 10 rpm to obtain a mixture. Magnesium stearate was passed through a 60-mesh screen, added to the mixture and lubricated in a blender for 10 minutes at 10 rpm to obtain a blend for compaction.

Step 4: The blend from step 3 was compacted in a roller compactor. The roller compaction process parameters are mentioned in Table 4B to obtain compacts, which were milled and passed through a 30-mesh screen to obtain granules.

Step 5: Microcrystalline cellulose and croscarmellose sodium were weighed, passed through a 40-mesh screen and blended with the granules from step 4 for 10 minutes at 10 rpm to obtain a pre-lubricated blend.

Step 6 (Lubrication): Magnesium stearate was passed through a 60-mesh screen, added to the pre-lubricated blend of step 5, and lubricated for 15 minutes at 10 rpm to obtain final blend.

Step 7: The final blend was compressed into a tablet and coated with OPADRY® II white 85F18422 aqueous dispersion.

Any suitable operating parameters conditions may be used for the above steps. For instance, the spray drying may be carried out using the parameters set forth in Table 4A.

TABLE 4A

| Parameters | Typical value | Typical ranges |
| --- | --- | --- |
| Total dissolved solids | 5% | 3-7% |
| Inlet Temperature (° C.) | 75-77 | 70-80 |
| Outlet Temperature (° C.) | 47-52 | 40-60 |
| Atomization pressure (kg/cm$^2$) | 1.23-1.24 | 1.1-1.3 |
| Inlet air (m$^3$/hr) | 80 | 75-85 |
| Feed rate (mL/min) | 5-7 | 4-8 |

Any suitable operating parameters conditions may be used for the above steps. For instance, the roller compaction may be carried out using the following the parameters set forth in Table 4B.

TABLE 4B

| Roller compaction process parameters | Range |
| --- | --- |
| Pre-granulator screen (mm) | 1.6 |
| Fine granulator screen (mm) | 1 |
| Screw feeder (rpm) | 27-33 |
| Fine granulator (rpm) | 50-100 |
| Roller speed (rpm) | 4-8 |
| Roller gap (mm) | 1-4 |
| Hydraulic pressure (Bar) | 40-100 |
| Vacuum | On |
| Roller gap control | On |
| Flake crusher | On |

Example 3

Hot-melt extruded formulations containing enteric polymer, soluble polymer and optional surfactant were prepared, having the compositions set forth in Table 5.

TABLE 5

| | Composition | |
| --- | --- | --- |
| Component | 3 mg/unit | 4 mg/unit |
| Granules of Extrudate: | | |
| Lurasidone | 37.2 | 37.2 |
| HPMC-AS | 111.7 | 111.7 |
| Hydroxypropyl cellulose | 22.3 | 22.3 |
| Sodium lauryl sulfate | 9.3 | — |
| Extra-granular Material: | | |
| Microcrystalline cellulose (Avicel PH 102) | 139.04 | 139.04 |
| Croscarmellose sodium (Ac-Di-Sol) | 9 | 9 |
| Aerosil Pharma 200 | 1.5 | 1.5 |
| Magnesium Stearate | 1.5 | 1.5 |
| Total weight | 331.54 | 322.24 |
| Coating: | | |
| OPADRY ® II white | 9.93 | 9.66 |
| Total weight of film-coated tablet | 341.47 | 331.9 |

Manufacturing Procedure:

Lurasidone (free base), HPMC-AS, hydroxypropyl cellulose, and optionally sodium lauryl sulfate were weighed in the quantities as shown in Table 5, and physically mixed in a polybag. The mixture was then placed in an extruder hopper. The Omicron 10P extruder used has a single screw solid conveying mechanism that extends from the hopper through multiple heating zones to the extrusion die. The mixture was passed through the heated extruder at a temperature range from about 29° C. to about 170° C., as determined by temperature setting of the extruder heating zones so that melting or softening of the mixture occurred. An extruder torque and screw speed were used as shown in Table 2. The resulting extrudate was cooled to room temperature and crushed. Then the crushed material was passed through a 40-mesh screen.

Microcrystalline cellulose, croscarmellose sodium, and Aerosil were passed through a 40-mesh screen and added to a blender. The granules of the extrudate were added to a blender and blended for 10 minutes at 10 rpm to obtain a pre-lubricated blend. Magnesium stearate was sifted through a 60-mesh screen and added to the pre-lubricated blend in the blender, and blended for 5 minutes at 10 rpm to obtain a lubricated blend. The lubricated blend was compressed into tablets.

The tablets were coated with OPADRY® II white 85F18422 aqueous dispersion.

Example 4

An open-label, balanced, randomized, single-dose, two-treatment, three-period, three-sequence, three-way crossover oral relative bioavailability study of Composition 1 and the lurasidone drug product sold under the trademark LATUDA® tablets (40 mg) was conducted in 21 normal, healthy, adult human subjects, under fasting and fed conditions.

TABLE 6

| Pharmaco-kinetic parameter | Composition 1 (Fast) | LATUDA ® (Fed) | Composition 1 (Fast)/ LATUDA ® (Fed) (%) | 90% CI |
| --- | --- | --- | --- | --- |
| $C_{max}$ (ng/mL) | 74.33 | 89.07 | 83.45 | 71.88-96.88 |
| $AUC_{0-t}$ (ng · hr/mL) | 305.5 | 418.68 | 72.97 | 66.67-79.86 |
| $AUC_{0-\infty}$ (ng · hr/mL) | 329.45 | 463.14 | 71.13 | 64.89-77.99 |

TABLE 7

| Pharmaco-kinetic parameter | Composition 1 (Fed) | LATUDA ® (Fed) | Composition 1 (Fed)/ LATUDA ® (Fed) (%) | 90% CI |
| --- | --- | --- | --- | --- |
| $C_{max}$ (ng/mL) | 80.12 | 89.07 | 89.95 | 77.49-104.41 |
| $AUC_{0-t}$ (ng · hr/mL) | 425.78 | 418.68 | 101.7 | 93.97-110.06 |
| $AUC_{0-\infty}$ (ng · hr/mL) | 459.85 | 462.12 | 99.51 | 91.45-108.27 |

TABLE 8

| Pharmaco-kinetic parameter | N | Composition 1 Fast | Composition 1 Fed | Composition 1 fast/fed (%) | 90% CI |
|---|---|---|---|---|---|
| $C_{max}$ (ng/mL) | 16 | 74.33 | 80.12 | 92.77 | 78.80-109.24 |
| $AUC_{0-t}$ (ng · hr/mL) | 16 | 305.5 | 425.78 | 71.76 | 64.69-79.58 |
| $AUC_{0-\infty}$ (ng · hr/mL) | 13 | 329.45 | 459.85 | 71.64 | 63.81-79.19 |

Example 5

A study was conducted to test the pharmacokinetics and bioavailability of a Composition 2 in healthy human subjects, with the subjects in either a fed or a fasted state. The effect of food on bioavailability from a single oral dose of the lurasidone hydrochloride tablet of composition 2 was evaluated.

An open-label, balanced, randomized, single-dose, two-treatment, three-period, three-sequence, three-way cross-over oral relative bioavailability study of Composition 2 and LATUDA® tablets 40 mg was conducted in 21 normal, healthy, adult, human subjects under fasting and fed conditions.

TABLE 9

| Pharmaco-kinetic parameter | Composition 2 (Fast) | LATUDA® (Fed) | Composition 2 (fast)/ LATUDA® (Fed) (%) | 90% CI |
|---|---|---|---|---|
| $C_{max}$ (ng/mL) | 94.42 | 109.46 | 86.27 | 72.43-102.74 |
| $AUC_{0-t}$ (ng · hr/mL) | 308.6 | 442.51 | 69.74 | 63.34-76.78 |
| $AUC_{0-\infty}$ (ng · hr/mL) | 331.24 | 480.95 | 68.87 | 62.64-75.72 |

TABLE 10

| Pharmaco-kinetic parameter | Composition 2 (Fed) | LATUDA® (Fed) | Composition 2 (Fed)/ LATUDA® (Fed) (%) | 90% CI |
|---|---|---|---|---|
| $C_{max}$ (ng/mL) | 75.28 | 109.46 | 68.77 | 60.59-78.06 |
| $AUC_{0-t}$ (ng · hr/mL) | 400.00 | 442.51 | 90.39 | 84.26-96.97 |
| $AUC_{0-\infty}$ (ng · hr/mL) | 430.87 | 480.95 | 89.59 | 83.58-96.02 |

TABLE 11

| PK parameter | N | Composition 2 Fast | Composition 2 Fed | Composition 2 fast/fed (%) | 90% CI |
|---|---|---|---|---|---|
| $C_{max}$ (ng/mL) | 20 | 94.42 | 75.28 | 125.43 | 104.61-150.40 |
| $AUC_{0-t}$ (ng · hr/mL) | 20 | 308.6 | 400.00 | 77.15 | 71.06-83.77 |
| $AUC_{0-\infty}$ (ng · hr/mL) | 18 | 331.24 | 430.87 | 76.88 | 70.90-83.36 |

Example 6

Dissolution profiles of LATUDA® tablets and Composition 2 in 0.01N HCl acid media, followed by FaSSIF media of pH 6.5

Figure 4:
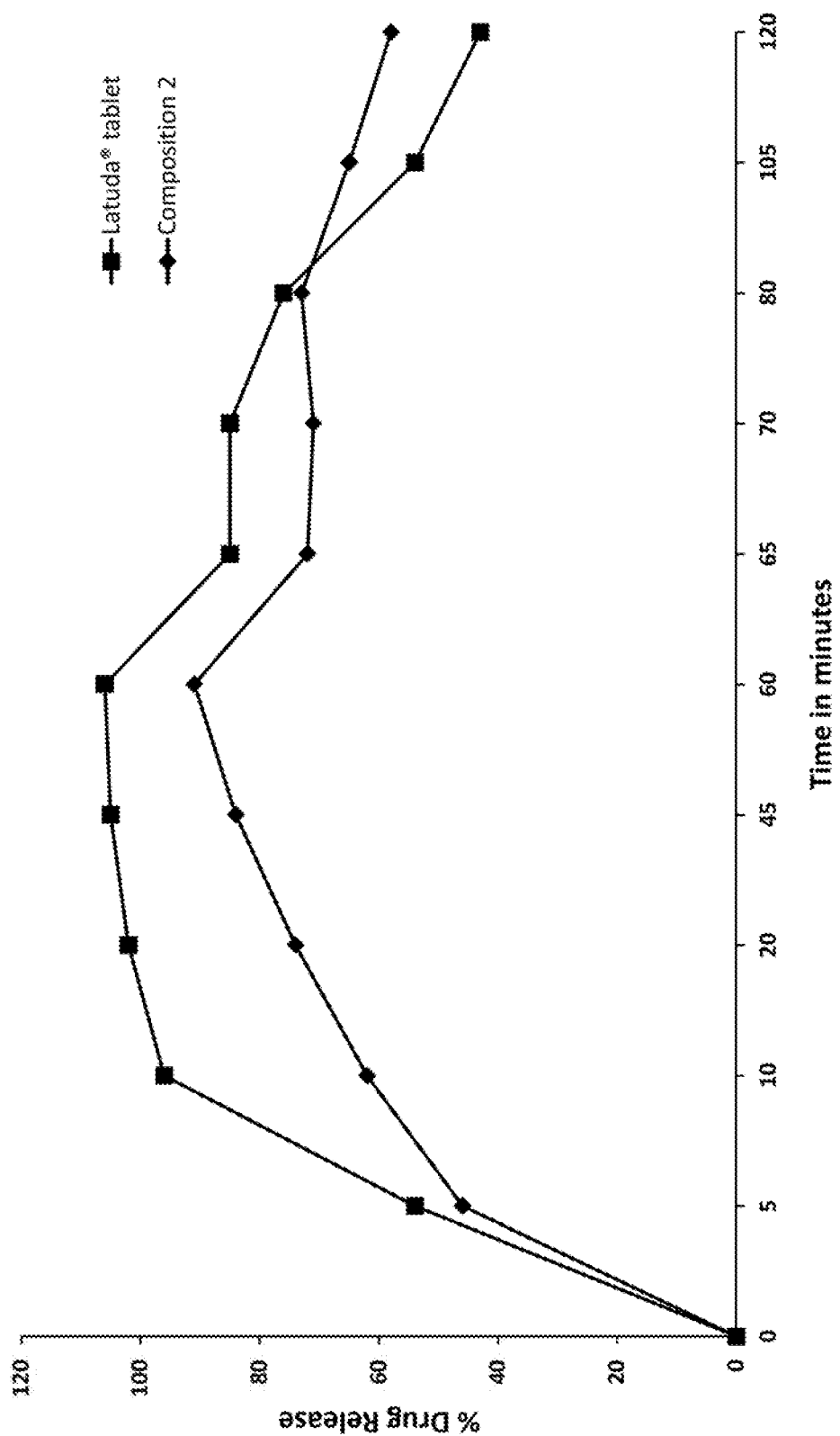
FIG. 4 illustrates comparative dissolution profiles graph of LATUDA® tablet and composition 2 in 0.01N HCl followed by FaSSIF media at pH 6.5.

Dissolution analysis was carried out in a USP type II dissolution bath (VanKel) using 500 mL of 0.01N HCl kept at 37° C. for 60 minutes and followed by 500 mL FaSSIF media of pH 6.5 for 60 minutes at 37° C. and stirred at 75 rpm. Samples were taken at 5, 10, 20, 45, and 60 minutes from 0.01N HCl media and 65, 70, 80, 105 and 120 minute time points from FaSSIF media of pH 6.5 and analyzed using HPLC system with UV spectrophotometer at a wavelength 232 nm. The results of the measurements are given in Table 12 and shown graphically in FIG. 4.

TABLE 12

| Dissolution Media | Time in minutes | % of Drug released LATUDA® | % of Drug released Composition 2 |
|---|---|---|---|
| Acid media (0.01N HCl media) | 0 | 0 | 0 |
| | 5 | 54 | 46 |
| | 10 | 96 | 62 |
| | 20 | 102 | 74 |
| | 45 | 105 | 84 |
| | 60 | 106 | 91 |
| FaSSIF media of pH 6.5 | 65 | 85 | 72 |
| | 70 | 85 | 71 |
| | 80 | 76 | 73 |
| | 105 | 54 | 65 |
| | 120 | 43 | 58 |

Dissolution Profiles of LATUDA® Tablets and Composition 2 in 0.01N HCl Acid Media, Followed by FeSSIF Media of pH 5.0

Figure 5:
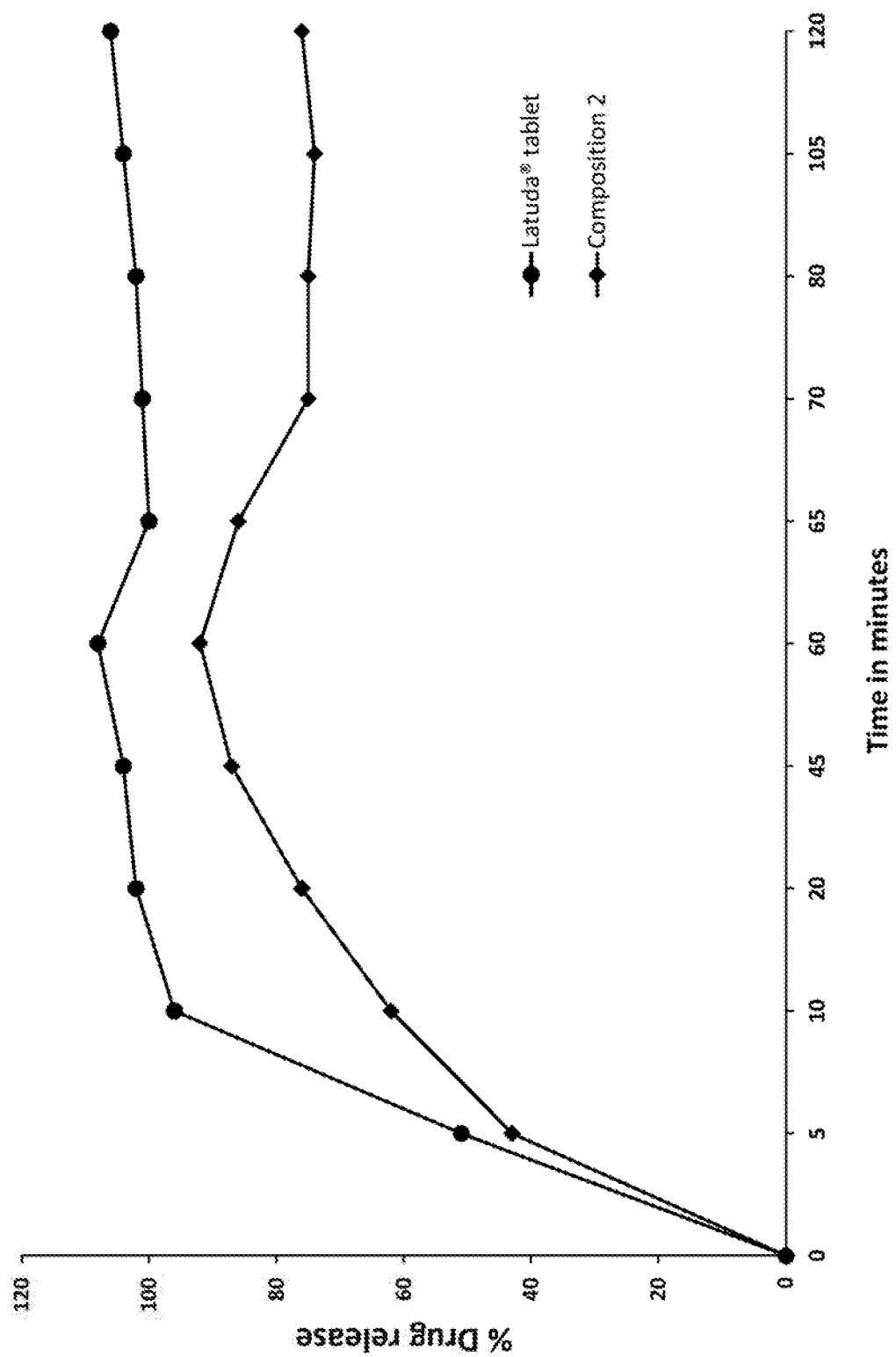
FIG. 5 illustrates comparative dissolution profiles graph of LATUDA® tablet and composition 2 in 0.01N HCl followed by FeSSIF media at pH 5.0.

Dissolution analysis was carried out in a USP type II dissolution bath (VanKel) using 500 mL of 0.01N HCl kept at 37° C. for 60 minutes and followed by 500 mL FeSSIF media of pH 5.0 for 60 minutes at 37° C. and stirred at 75 rpm. Samples were taken at 5, 10, 20, 45, and 60 minutes from 0.01N HCl media and 65, 70, 80, 105 and 120 minute time points from FeSSIF media of pH 5.0 and analyzed using HPLC system with UV spectrophotometer at a wavelength 232 nm. The results of the measurements are given in Table 13 and shown graphically in FIG. 5.

TABLE 13

| Dissolution Media | Time in minutes | % of Drug released LATUDA® | % of Drug released Composition 2 |
|---|---|---|---|
| Acid media (0.01N HCl media) | 0 | 0 | 0 |
| | 5 | 51 | 43 |
| | 10 | 96 | 62 |
| | 20 | 102 | 76 |
| | 45 | 104 | 87 |
| | 60 | 108 | 92 |
| FeSSIF media of pH 5.0 | 65 | 100 | 86 |
| | 70 | 101 | 75 |
| | 80 | 102 | 75 |
| | 105 | 104 | 74 |
| | 120 | 106 | 76 |

Example 7

Dissolution Profiles of LATUDA® Tablets, Compositions 1, 3 and 4 in 0.01N HCl Acid Media, Followed by FaSSIF Media of pH 6.5

Figure 6:
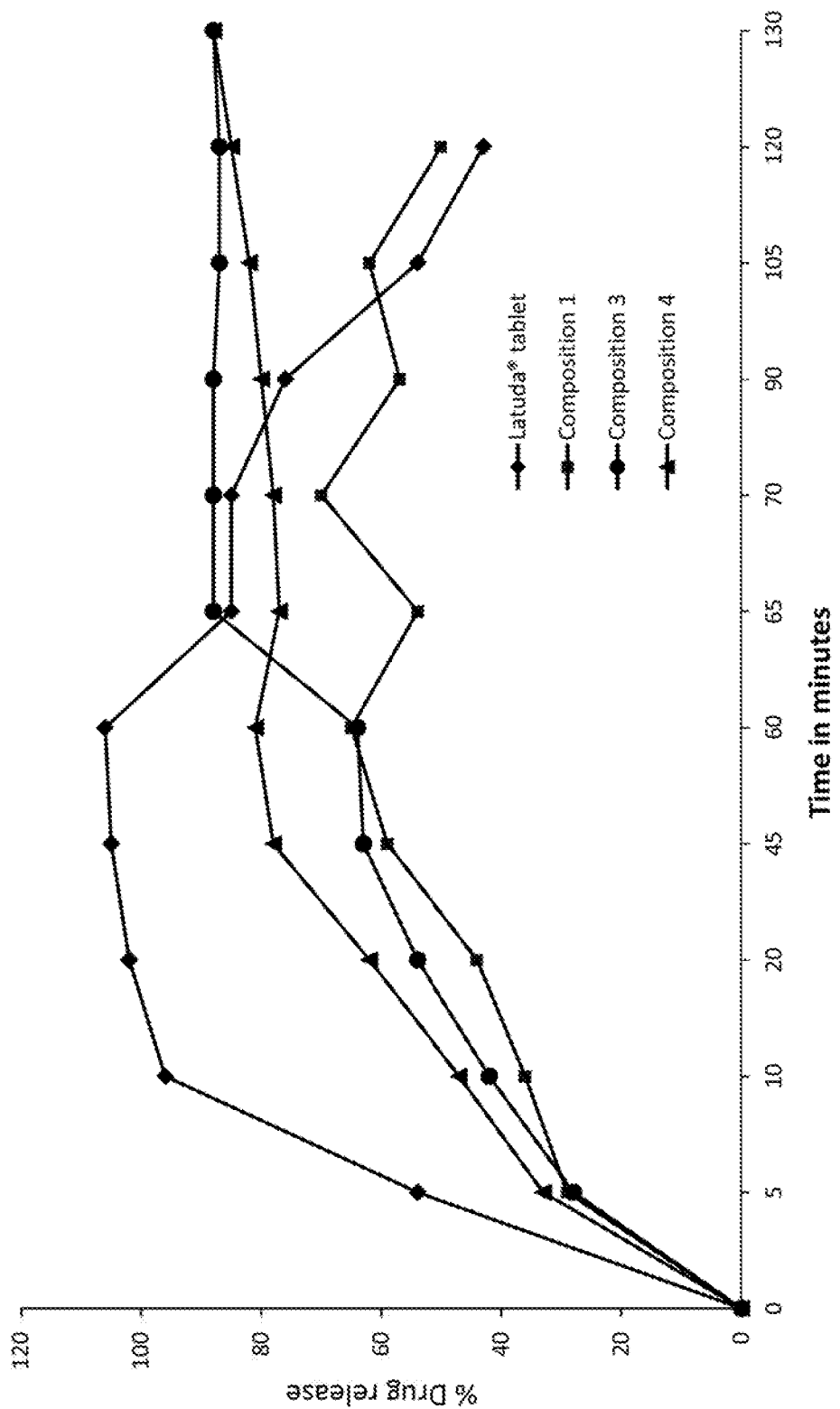
FIG. 6 illustrates comparative dissolution profiles graph of LATUDA® tablet and compositions 1, 3 and 4 in 0.01N HCl followed by FaSSIF media at pH 6.5.

Dissolution analysis was carried out in a USP type II dissolution bath (VanKel) using 500 mL of 0.01N HCl kept at 37° C. for 60 minutes and followed by 500 mL FaSSIF media of pH 6.5 for 60 minutes at 37° C. and stirred at 75 rpm. Samples were taken at 5, 10, 20, 45, and 60 minutes from 0.01N HCl media and 65, 70, 90, 105 and 120 minute time points from FaSSIF media of pH 6.5 and analyzed using HPLC system with UV spectrophotometer at a wavelength 232 nm. The results of the measurements are given in Table 14 and shown graphically in FIG. 6.

TABLE 14

| Dissolution Media | Time (minutes) | % of Drug released | | | |
|---|---|---|---|---|---|
| | | Latuda ® | Composition 1 | 3 | 4 |
| Acid media (0.01N HCl media) | 0 | 0 | 0 | 0 | 0 |
| | 5 | 54 | 29 | 28 | 33 |
| | 10 | 96 | 36 | 42 | 47 |
| | 20 | 102 | 44 | 54 | 62 |
| | 45 | 105 | 59 | 63 | 78 |
| | 60 | 106 | 65 | 64 | 81 |
| FaSSIF media (pH 5.0) | 65 | 85 | 54 | 88 | 77 |
| | 70 | 85 | 70 | 88 | 78 |
| | 90 | 76 | 57 | 88 | 80 |
| | 105 | 54 | 62 | 87 | 82 |
| | 120 | 43 | 50 | 87 | 85 |
| | 130 | — | — | 88 | 88 |

Dissolution Profiles of LATUDA® Tablets and Composition 1 in 0.01N HCl Acid Media, Followed by FeSSIF Media of pH 5.0

Figure 7:
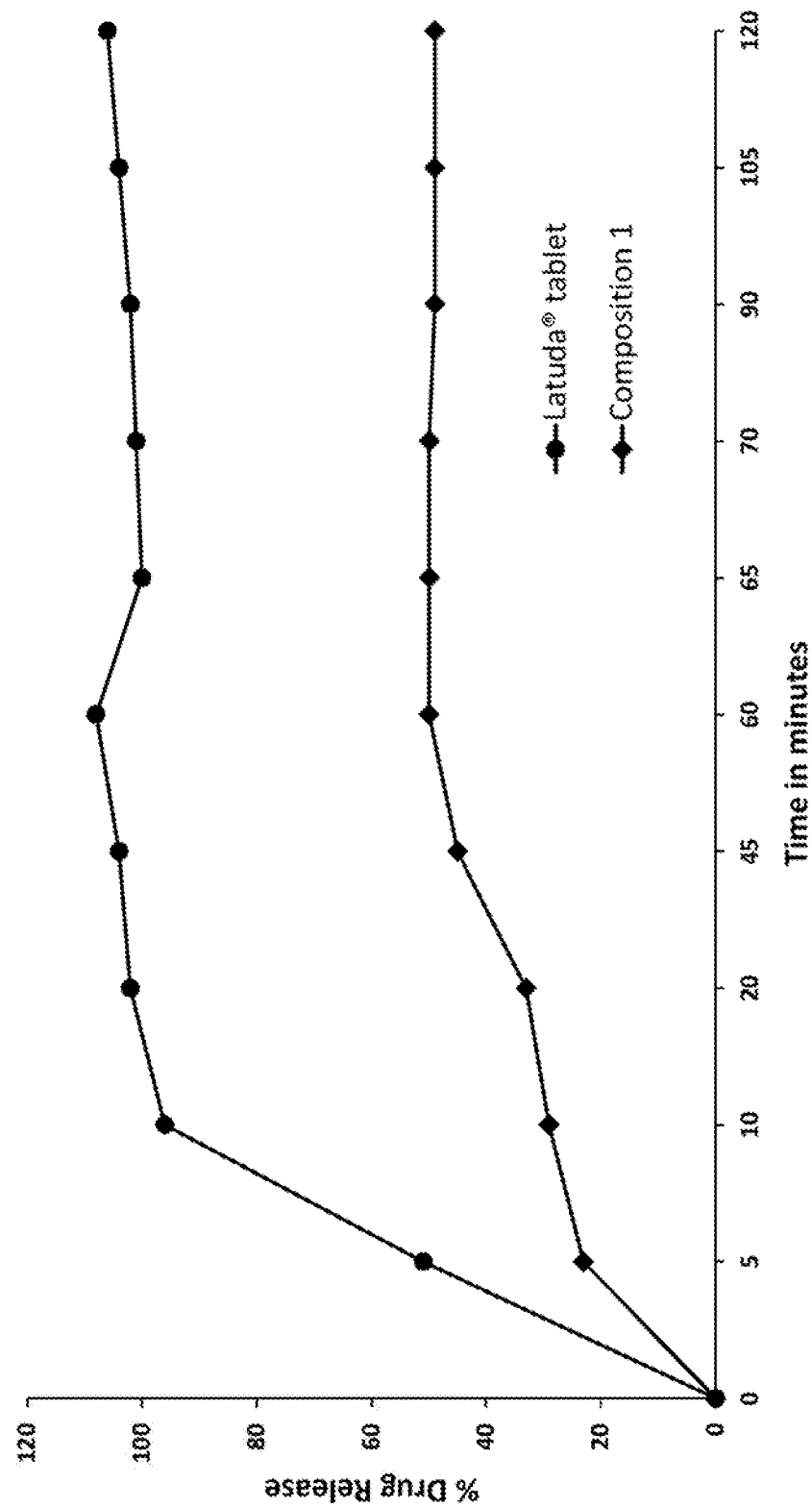
FIG. 7 illustrates comparative dissolution profiles graph of LATUDA® tablet and composition 1 in 0.01N HCl followed by FeSSIF media at pH 5.0.

Dissolution analysis was carried out in a USP type II dissolution bath (VanKel) using 500 mL of 0.01N HCl kept at 37° C. for 60 minutes and followed by 500 mL FeSSIF media of pH 5.0 for 60 minutes at 37° C. and stirred at 75 rpm. Samples were taken at 5, 10, 20, 45, and 60 minutes from 0.01N HCl media and 65, 70, 90, 105 and 120 minute time points from FeSSIF media of pH 5.0 and analysed using HPLC system with UV spectrophotometer at a wavelength 232 nm. The results of the measurements are given in Table 15 and shown graphically in FIG. 7.

TABLE 15

| Dissolution Media | Time in minutes | % of Drug released | |
|---|---|---|---|
| | | Latuda ® | Composition 1 |
| Acid media (0.01N HCl media) | 0 | 0 | 0 |
| | 5 | 51 | 23 |
| | 10 | 96 | 29 |
| | 20 | 102 | 33 |
| | 45 | 104 | 45 |
| | 60 | 108 | 50 |
| FeSSIF media of pH 5.0 | 65 | 100 | 50 |
| | 70 | 101 | 50 |
| | 90 | 102 | 49 |
| | 105 | 104 | 49 |
| | 120 | 106 | 49 |

Example 8

Dissolution Profiles of Latuda Tablets, Compositions 1, 3 and 4 in McIlvaine Buffer Media of pH 6.5

Figure 8:
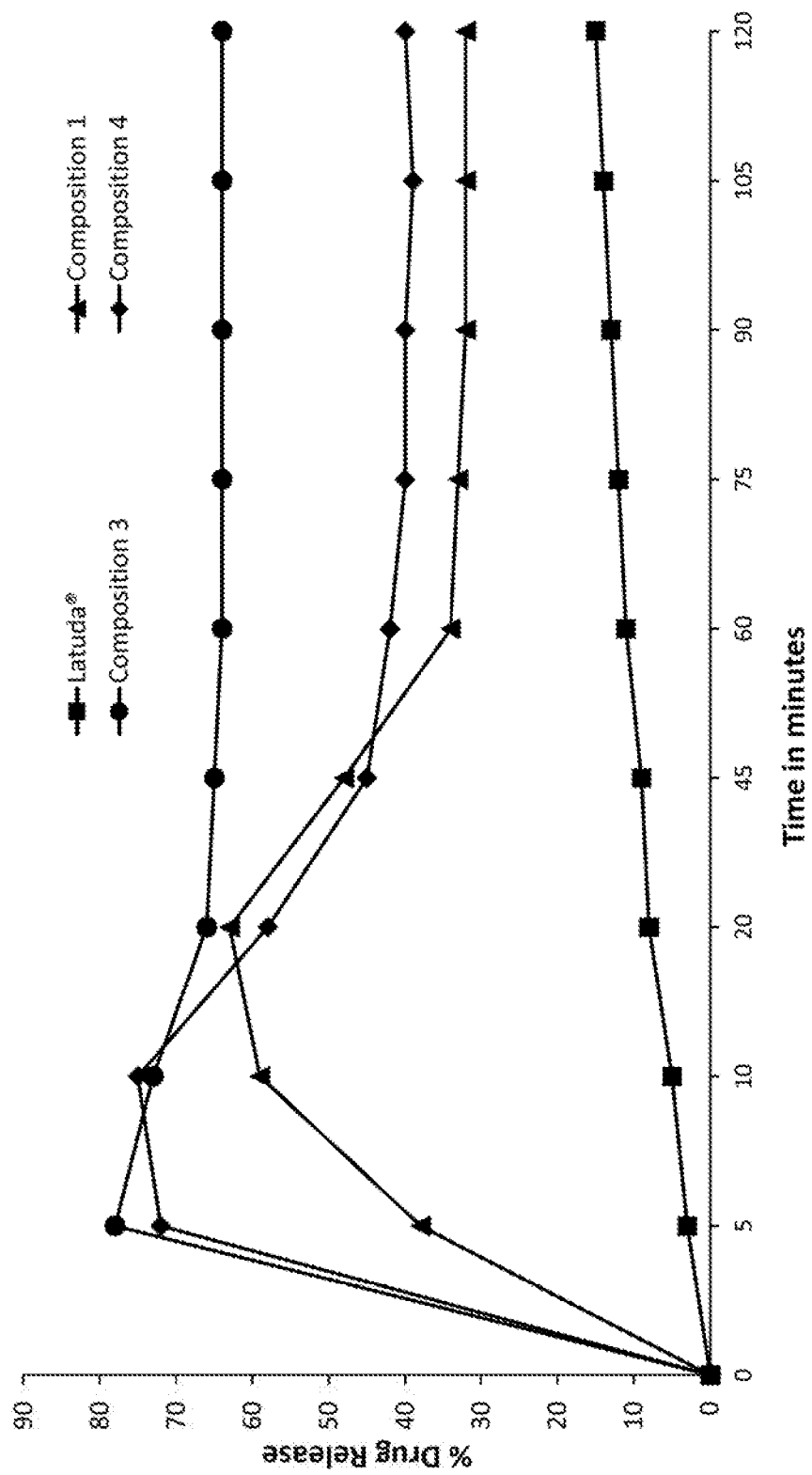
FIG. 8 illustrates comparative dissolution profiles graph of LATUDA® tablet and compositions 1, 3 and 4 in McIlvaine buffer at pH 6.5.

Dissolution analysis was carried out in a USP type II dissolution bath (VanKel) using 1000 mL of McIlvaine buffer media of pH 6.5 kept at 37° C. for 120 minutes and stirred at 75 rpm. Samples were taken at 5, 10, 20, 45, 60, 75, 90, 105 and 120 minutes and analysed using HPLC system with UV spectrophotometer at a wavelength 232 nm. The results of the measurements are given in Table 16 and shown graphically in FIG. 8.

TABLE 16

| Time in minutes | Latuda ® | Composition 1 | Composition 3 | Composition 4 |
|---|---|---|---|---|
| 0 | 0 | 0 | 0 | 0 |
| 5 | 3 | 38 | 78 | 72 |
| 10 | 5 | 59 | 73 | 75 |
| 20 | 8 | 63 | 66 | 58 |
| 45 | 9 | 48 | 65 | 45 |
| 60 | 11 | 34 | 64 | 42 |
| 75 | 12 | 33 | 64 | 40 |
| 90 | 13 | 32 | 64 | 40 |
| 105 | 14 | 32 | 64 | 39 |
| 120 | 15 | 32 | 64 | 40 |

Dissolution Profiles of LATUDA® Tablets, Composition 1, 3 and 4 in FaSSIF Media of pH 6.5

Figure 9:
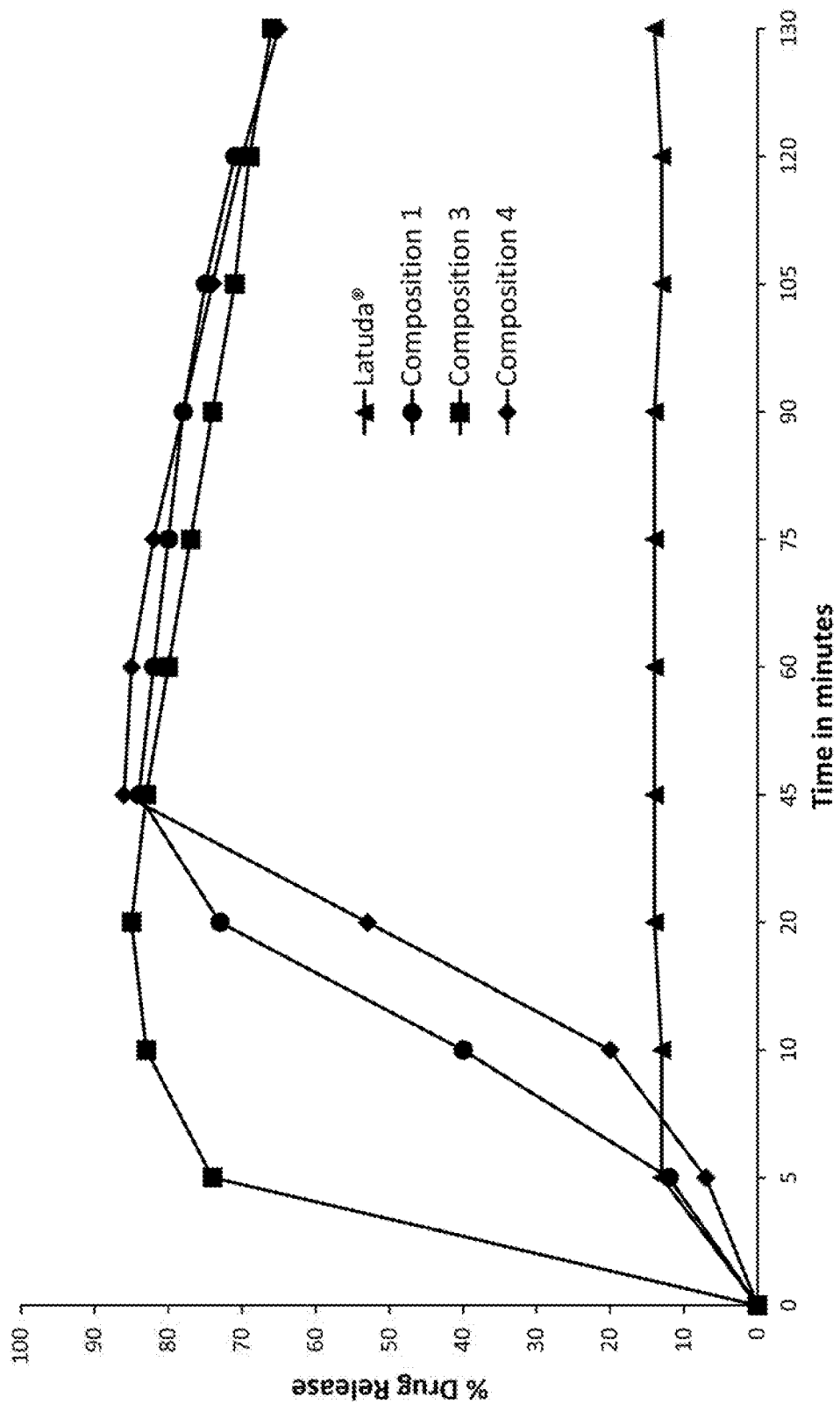
FIG. 9 illustrates comparative dissolution profiles graph of LATUDA® tablet and compositions 1, 3 and 4 in FaSSIF media at pH 6.5.

Dissolution analysis was carried out in a USP type II dissolution bath (VanKel) using 1000 mL of FaSSIF media of pH 6.5 kept at 37° C. for 120 minutes and stirred at 75 rpm. Samples were taken at 5, 10, 20, 45, 60, 75, 90, 105 and 120 minutes and analyzed using HPLC system with UV spectrophotometer at a wavelength 232 nm. The results of the measurements are given in Table 17 and shown graphically in FIG. 9.

TABLE 17

| Time in minutes | LATUDA ® | Composition 1 | Composition 3 | Composition 4 |
|---|---|---|---|---|
| 0 | 0 | 0 | 0 | 0 |
| 5 | 13 | 12 | 74 | 7 |
| 10 | 13 | 40 | 83 | 20 |
| 20 | 14 | 73 | 85 | 53 |
| 45 | 14 | 84 | 83 | 86 |
| 60 | 14 | 82 | 80 | 85 |
| 75 | 14 | 80 | 77 | 82 |
| 90 | 14 | 78 | 74 | 78 |
| 105 | 13 | 75 | 71 | 74 |
| 120 | 13 | 71 | 69 | 70 |
| 130 | 14 | — | 66 | 65 |

Figure 10:
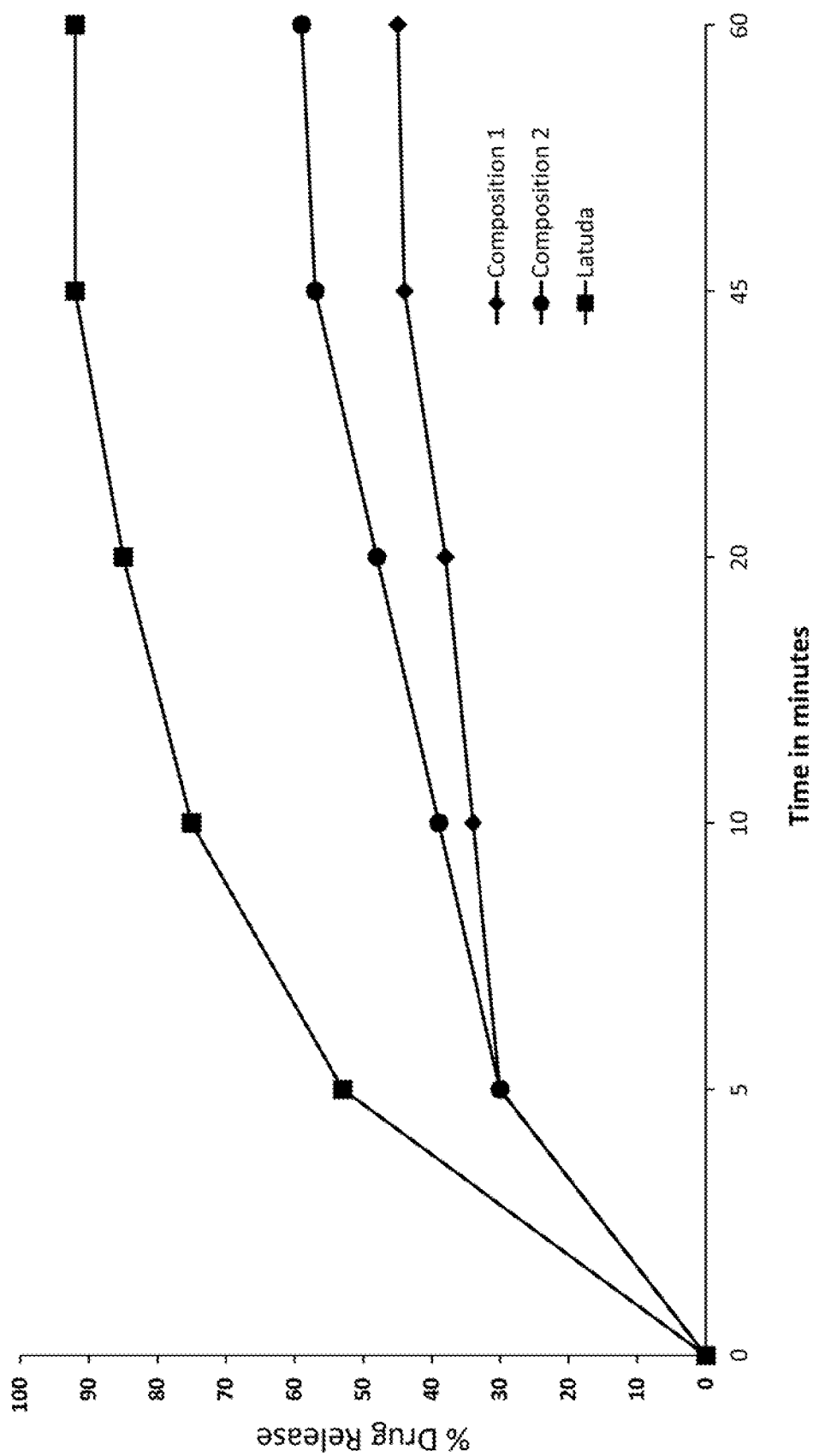
FIG. 10 illustrates comparative dissolution profiles graph of LATUDA® tablet and compositions 1 and 2 in 0.1 N HCl.

Dissolution Profiles of LATUDA® Tablets, Compositions 1 and 2 in 0.1N HCl Acid Media Dissolution analysis was carried out in a USP type II dissolution bath (VanKel) using 500 mL of 0.1 N HCl acid media kept at 37° C. for 60 minutes and stirred at 75 rpm. Samples were taken at 5, 10, 20, 45 and 60 minutes and analyzed using HPLC system with UV spectrophotometer at a wavelength 232 nm. The results of the measurements are given in Table 18 and shown graphically in FIG. 10.

TABLE 18

| Time in minutes | Composition 1 | Composition 2 | LATUDA ® |
|---|---|---|---|
| 0 | 0 | 0 | 0 |
| 5 | 30 | 30 | 53 |
| 10 | 34 | 39 | 75 |
| 20 | 38 | 48 | 85 |
| 45 | 44 | 57 | 92 |
| 60 | 45 | 59 | 92 |

Dissolution Profiles of LATUDA® Tablets, Compositions 1 and 2 in Acetate Buffer of pH 4.5

Figure 11:
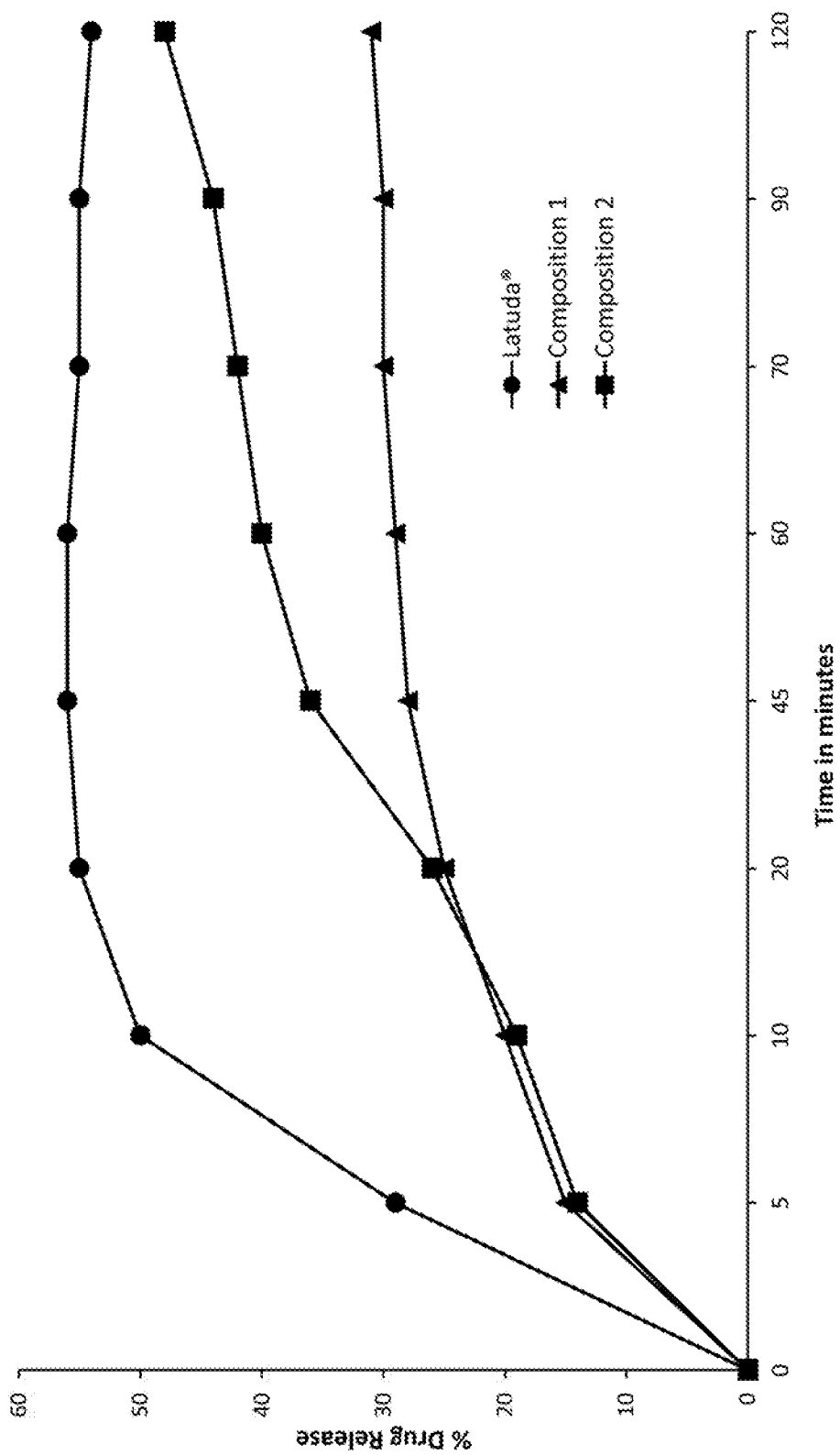
FIG. 11 illustrates comparative dissolution profiles graph of LATUDA® tablet and compositions 1 and 2 in acetate buffer at pH 4.5.

Dissolution analysis was carried out in a USP type II dissolution bath (VanKel) using 1000 mL of acetate buffer of pH 4.5 kept at 37° C. for 60 minutes and stirred at 75 rpm. Samples were taken at 5, 10, 20, 45, 60, 90 and 120 minutes and analyzed using HPLC system with UV spectrophotometer at a wavelength 232 nm. The results of the measurements are given in Table 19 and shown graphically in FIG. 11.

TABLE 19

| Time in minutes | LATUDA® | Composition 1 | Composition 2 |
|---|---|---|---|
| 0 | 0 | 0 | 0 |
| 5 | 29 | 15 | 14 |
| 10 | 50 | 20 | 19 |
| 20 | 55 | 25 | 26 |
| 45 | 56 | 28 | 36 |
| 60 | 56 | 29 | 40 |
| 70 | 55 | 30 | 42 |
| 90 | 55 | 30 | 44 |
| 120 | 54 | 31 | 48 |

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

Unless specified otherwise, all the percentages, portions and ratios in the present invention are on weight basis.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

While compositions and methods are described herein in terms of "comprising" various components or steps, the compositions and methods can also "consist essentially of" or "consist of" the various components and steps.

The invention claimed is:

1. A pharmaceutical composition comprising a solid dispersion of amorphous lurasidone or pharmaceutically acceptable salt thereof;
wherein the solid dispersion consists of amorphous lurasidone or pharmaceutically acceptable salt thereof, a pharmaceutically acceptable carrier, optionally a solubilizer, and optionally a surfactant;
wherein the pharmaceutically acceptable carrier is selected from the group consisting of hydroxypropyl methyl cellulose acetate succinate, a copolymer of polyvinyl pyrrolidone and vinyl acetate, hydroxypropyl cellulose, hydroxypropyl methylcellulose phthalate, and mixtures thereof;
wherein the solubilizer is selected from the group consisting of sorbitol, mannitol, polyvinyl alcohol, hydroxypropyl methylcellulose, hydroxypropyl cellulose, polyvinyl pyrrolidone, glycofurol and transcutol; and
wherein the surfactant is selected from the group consisting of anionic, nonionic, cationic, and zwitterionic surfactants;
further wherein the pharmaceutical composition is in the form of a tablet; and wherein the tablet comprises (a) granules of the solid dispersion of amorphous lurasidone or a pharmaceutically acceptable salt thereof, (b) at least one extra-granular excipient, and (c) optionally, a tablet coating;
wherein the at least one extra-granular excipient is selected from the group consisting of microcrystalline cellulose, croscarmellose sodium, colloidal silicon dioxide, magnesium stearate, and mixtures thereof;
wherein a peak plasma concentration of lurasidone or a pharmaceutically acceptable salt thereof in a fed state is within ±25% of a peak plasma concentration of lurasidone or a pharmaceutically acceptable salt thereof in a fasted state; and
wherein the pharmaceutical composition may be administered to a human subject without regard to food.

2. The pharmaceutical composition according to claim 1, wherein the solid dispersion of amorphous lurasidone is prepared by hot-melt extrusion, spray-drying or co-precipitation.

3. The pharmaceutical composition according to claim 1, wherein the solid dispersion of amorphous lurasidone has a weight ratio of the lurasidone or pharmaceutically acceptable salt thereof to the pharmaceutically acceptable carrier from about 1:1 to about 1:6.

4. The pharmaceutical composition according to claim 1, wherein the solid dispersion of amorphous lurasidone has a weight ratio of the lurasidone or pharmaceutically acceptable salt thereof to the pharmaceutically acceptable carrier from about 1:2 to about 1:4.

5. The pharmaceutical composition according to claim 1, wherein the solid dispersion of amorphous lurasidone has a weight ratio of the lurasidone or pharmaceutically acceptable salt thereof to the pharmaceutically acceptable carrier of about 1:3.

6. The pharmaceutical composition according to claim 1, wherein the pharmaceutical composition comprises from about 20 mg to about 400 mg of lurasidone or pharmaceutically acceptable salt thereof.

7. The pharmaceutical composition according to claim 6, wherein the granules of the solid dispersion of amorphous lurasidone comprise at least a first portion of granules comprising lurasidone and hydroxypropyl methyl cellulose acetate succinate, and at least a second portion of granules comprising lurasidone and a copolymer of polyvinyl pyrrolidone and vinyl acetate.

8. The pharmaceutical composition according to claim 6, wherein the tablet is obtained by direct compression, wet granulation or dry granulation.

9. The pharmaceutical composition according to claim 6, wherein the tablet further comprises at least one excipient selected from the group consisting of binders, solubilizers, disintegrating agents, lubricants, colorants, surfactants and mixtures thereof.

10. The pharmaceutical composition according to claim 6, wherein the granules of the solid dispersion comprise lurasidone, hydroxypropyl methyl cellulose acetate succinate, hydroxypropyl cellulose, and optionally, sodium lauryl sulfate.

11. The pharmaceutical composition according to claim 1, wherein the in vitro dissolution rate of said pharmaceutical composition is less than about 50% in 60 minutes, wherein the in vitro dissolution rate is determined using a USP paddle method of 75 rpm in 500 ml of 0.1 N HCl at 37° C.; or wherein the in vitro dissolution rate is determined using a USP paddle method of 75 rpm in 1000 ml of 4.5 pH acetate buffer at 37° C.

12. The pharmaceutical composition according to claim 6, wherein a peak plasma concentration of lurasidone or a pharmaceutically acceptable salt thereof in the fed state is within ±10% of a peak plasma concentration of lurasidone or a pharmaceutically acceptable salt thereof in the fasted state.

\* \* \* \* \*